US008193395B2

(12) United States Patent
Fenton et al.

(10) Patent No.: US 8,193,395 B2
(45) Date of Patent: Jun. 5, 2012

(54) BIOMASS TREATMENT PROCESS AND SYSTEM

(75) Inventors: Marcus Brian Mayhall Fenton, Cambridgeshire (GB); Jens Havn Thorup, Bury St. Edmunds (GB)

(73) Assignee: Pursuit Dynamics PLC, Huntington (GB)

(*) Notice: Subject to any disclaimer, the term of this patent is extended or adjusted under 35 U.S.C. 154(b) by 665 days.

(21) Appl. No.: 12/290,700

(22) Filed: Oct. 30, 2008

(65) Prior Publication Data
US 2009/0240088 A1 Sep. 24, 2009

(51) Int. Cl.
C07C 29/00 (2006.01)

(52) U.S. Cl. ...................................... 568/840

(58) Field of Classification Search ............... 568/840
See application file for complete search history.

(56) References Cited

U.S. PATENT DOCUMENTS

| | | |
|---|---|---|
| 1,004,770 A | 10/1911 | Galloway |
| 1,289,812 A | 12/1918 | Kinney |
| 1,592,448 A | 7/1926 | Debus |
| 2,083,801 A | 6/1937 | Eddy |
| 2,396,290 A | 3/1949 | Schwarz |
| 2,971,325 A | 2/1961 | Gongwer |
| 3,259,320 A | 7/1966 | Christian |
| 3,265,027 A | 8/1966 | Brown |
| 3,304,564 A | 10/1967 | Green et al. |
| 3,402,555 A | 9/1968 | Piper |
| 3,411,301 A | 11/1968 | Olsen |
| 3,456,871 A | 7/1969 | Gosling |
| 3,493,181 A | 2/1970 | Goodnight et al. |
| 3,493,191 A | 2/1970 | Hughes |
| 3,529,320 A | 9/1970 | Kerns et al. |
| 3,664,768 A | 5/1972 | Mays et al. |
| 3,799,195 A | 3/1974 | Hermans |
| 3,823,929 A | 7/1974 | Rymarchyk et al. |
| 3,889,623 A | 6/1975 | Arnold |
| 3,984,504 A | 10/1976 | Pick |
| 4,014,961 A | 3/1977 | Popov |
| 4,072,470 A | 2/1978 | Tsuto et al. |
| 4,101,246 A | 7/1978 | Erickson |
| 4,157,304 A | 6/1979 | Molvar |
| 4,175,706 A | 11/1979 | Gerstmann |
| 4,192,465 A | 3/1980 | Hughes |
| 4,201,596 A | 5/1980 | Burroughs et al. |
| 4,212,168 A | 7/1980 | Bouchard et al. |
| 4,221,558 A | 9/1980 | Santisi |
| 4,279,663 A | 7/1981 | Burroughs et al. |
| 4,425,433 A | 1/1984 | Neves |
| 4,461,648 A | 7/1984 | Foody |
| 4,487,553 A | 12/1984 | Nagata |
| 4,659,521 A | 4/1987 | Alleman |
| 4,718,870 A | 1/1988 | Watts |
| 4,738,614 A | 4/1988 | Snyder et al. |
| 4,809,911 A | 3/1989 | Ryan |
| 4,836,451 A | 6/1989 | Herrick et al. |
| 4,915,300 A | 4/1990 | Ryan |
| 4,915,302 A | 4/1990 | Kraus et al. |
| 5,014,790 A | 5/1991 | Papavergos |
| 5,061,406 A | 10/1991 | Cheng |
| 5,138,937 A | 8/1992 | Zietlow |
| 5,171,090 A | 12/1992 | Wiemers |
| 5,205,648 A | 4/1993 | Fissenko |
| 5,240,724 A | 8/1993 | Otto et al. |
| 5,249,514 A | 10/1993 | Otto et al. |
| 5,252,298 A | 10/1993 | Jones |
| 5,269,461 A | 12/1993 | Davis |
| 5,275,486 A | 1/1994 | Fissenko |
| 5,312,041 A | 5/1994 | Williams et al. |
| 5,323,967 A | 6/1994 | Tanaka et al. |
| 5,338,113 A | 8/1994 | Fissenko |
| 5,344,345 A | 9/1994 | Nagata |
| 5,366,288 A | 11/1994 | Dahllof et al. |
| 5,492,276 A | 2/1996 | Kaylor |
| 5,495,893 A | 3/1996 | Roberts et al. |
| 5,520,331 A | 5/1996 | Wolfe |
| 5,544,961 A | 8/1996 | Fuks et al. |
| 5,597,044 A | 1/1997 | Roberts et al. |

(Continued)

FOREIGN PATENT DOCUMENTS

CA 833980 2/1970

(Continued)

OTHER PUBLICATIONS

Patent Abstracts of Japan, vol. 016, No. 496 (M-1325), Oct. 15, 1992 & JP 04 184000 A (Mitsui Eng & Shipbuild Co Ltd), Jun. 30, 1992.
Patent Abstracts of Japan, vol. 2002, No. 4, Aug. 4, 2002 & JP 2001 354319 A (Ogawa Jidosha:KK), Dec. 25. 2001.
Final Scientific Report, "New Regenerative Cycle for Vapor Compression Refrigeration", DE-FG36-04GO14327 Sep. 30, 2004 to Sep. 30, 2005.
Cincotta, "From the Lab to Production: Direct Steam Injection Heating of Fibrous Slurries", Biomass Magazine, Jul. 1, 2008.
Khanal, et al., "Ultrasound Enhanced Glucose Release From Corn in Ethanol Plants", Biotechnology and Bioengineering, vol. 98, No. 5, pp. 978-985, Dec. 1, 2007.
Hagen, Energy economy by continuous steaming and mashing, International Food Information Service (IFIS), Frankfurt-Main, DE (1984).

(Continued)

Primary Examiner — Sikarl Witherspoon
(74) Attorney, Agent, or Firm — Bryan Cave LLP

(57) ABSTRACT

The present invention provides processes and systems for treating biomass and, e.g., making biofuels, such as bioethanol, from the biomass. More particularly, one process according to the present invention includes (a) inducing at least a first portion of a composition containing biomass and a working fluid to flow into a passage of a fluid processing apparatus, (b) injecting a high velocity transport fluid into the composition through a nozzle communicating with the passage of the fluid processing apparatus, whereby the transport fluid applies a shear force to the composition such that the working fluid is atomized and a vapor and droplet flow regime is formed downstream of the nozzle, (c) condensing the vapor and droplet flow regime, (d) transferring the composition to a first holding vessel, and (e) holding the composition in the first holding vessel at a first predetermined temperature for a first predetermined period of time, wherein a liquefaction enzyme is added to the composition prior to or during the process. Thereafter, the composition may be further processed to form a biofuel, such as, e.g., bioethanol.

48 Claims, 5 Drawing Sheets

U.S. PATENT DOCUMENTS

| | | | |
|---|---|---|---|
| 5,598,700 A | 2/1997 | Varshay et al. |
| 5,615,836 A | 4/1997 | Graef |
| 5,661,968 A | 9/1997 | Gabriel |
| 5,692,371 A | 12/1997 | Varshay et al. |
| 5,738,762 A | 4/1998 | Ohsol |
| 5,779,159 A | 7/1998 | Williams et al. |
| 5,810,252 A | 9/1998 | Pennamen et al. |
| 5,851,139 A | 12/1998 | Xu |
| 5,857,773 A | 1/1999 | Tammelin |
| 5,860,598 A | 1/1999 | Cruz |
| 5,863,128 A | 1/1999 | Mazzei |
| 6,003,789 A | 12/1999 | Base et al. |
| 6,029,911 A | 2/2000 | Watanabe et al. |
| 6,065,683 A | 5/2000 | Akin et al. |
| 6,098,896 A | 8/2000 | Haruch |
| 6,110,356 A | 8/2000 | Hedrick et al. |
| 6,200,486 B1 | 3/2001 | Chahine et al. |
| 6,299,343 B1 | 10/2001 | Pekerman |
| 6,308,740 B1 | 10/2001 | Smith et al. |
| 6,338,444 B1 | 1/2002 | Swan |
| 6,371,388 B2 | 4/2002 | Utter et al. |
| 6,405,944 B1 | 6/2002 | Benalikhoudja |
| 6,456,871 B1 | 9/2002 | Hsu et al. |
| 6,478,240 B1 | 11/2002 | Dorkin et al. |
| 6,502,979 B1 | 1/2003 | Kozyuk |
| 6,503,461 B1 | 1/2003 | Burgard et al. |
| 6,523,991 B1 | 2/2003 | Maklad |
| 6,623,154 B1 | 9/2003 | Garcia |
| 6,637,518 B1 | 10/2003 | Hillier et al. |
| 6,662,549 B2 | 12/2003 | Burns |
| 6,796,704 B1 | 9/2004 | Lott |
| 6,802,638 B2 | 10/2004 | Allen |
| 6,830,368 B2 | 12/2004 | Fukano |
| 6,969,012 B2 | 11/2005 | Kangas et al. |
| 7,029,165 B2 | 4/2006 | Allen |
| 7,040,551 B2 | 5/2006 | Rummel |
| 7,080,793 B2 | 7/2006 | Borisov et al. |
| 7,111,975 B2 | 9/2006 | Fenton et al. |
| 7,207,712 B2 | 4/2007 | Kozyuk |
| 7,667,082 B2 | 2/2010 | Kozyuk |
| 2002/0162518 A1 | 11/2002 | Dumaz et al. |
| 2003/0147301 A1 | 8/2003 | Ekholm |
| 2003/0150624 A1 | 8/2003 | Rummel |
| 2004/0065589 A1 | 4/2004 | Jorgensen |
| 2004/0141410 A1 | 7/2004 | Fenton et al. |
| 2004/0188104 A1 | 9/2004 | Borisov et al. |
| 2004/0222317 A1 | 11/2004 | Huffman |
| 2005/0000700 A1 | 1/2005 | Sundholm |
| 2005/0011355 A1 | 1/2005 | Williams et al. |
| 2005/0150971 A1 | 7/2005 | Zhou |
| 2005/0266539 A1 | 12/2005 | Hochberg et al. |
| 2006/0102351 A1 | 5/2006 | Crabtree et al. |
| 2006/0102749 A1 | 5/2006 | Crabtree et al. |
| 2006/0144760 A1 | 7/2006 | Duyvesteyn et al. |
| 2007/0000700 A1 | 1/2007 | Switzer |
| 2007/0095946 A1 | 5/2007 | Ryan |
| 2007/0128095 A1 | 6/2007 | Brockmann et al. |
| 2007/0210186 A1 | 9/2007 | Fenton et al. |
| 2008/0230632 A1 | 9/2008 | Fenton et al. |
| 2008/0310970 A1 | 12/2008 | Fenton et al. |
| 2009/0052275 A1 | 2/2009 | Jansson |
| 2009/0072041 A1 | 3/2009 | Hashiba |
| 2009/0314500 A1 | 12/2009 | Fenton et al. |
| 2010/0085833 A1 | 4/2010 | Zaiser |
| 2010/0129888 A1 | 5/2010 | Thorup et al. |
| 2010/0230119 A1 | 9/2010 | Worthy |
| 2010/0233769 A1 | 9/2010 | Heathcote et al. |
| 2010/0301129 A1 | 12/2010 | Fenton et al. |

FOREIGN PATENT DOCUMENTS

| | | |
|---|---|---|
| CN | 2356760 | 1/2000 |
| DE | 3316233 | 11/1984 |
| EP | 0362052 | 10/1991 |
| EP | 0471321 | 11/1995 |
| EP | 282061 | 3/1998 |
| EP | 0889244 | 1/1999 |
| EP | 0911082 | 4/1999 |
| EP | 1072320 | 1/2001 |
| EP | 1163931 | 12/2001 |
| EP | 1034029 | 3/2003 |
| EP | 1421996 | 5/2004 |
| EP | 1549856 | 6/2007 |
| EP | 2070881 | 6/2009 |
| FR | 474 904 | 3/1915 |
| FR | 1354965 | 3/1964 |
| FR | 2376384 | 7/1978 |
| FR | 2613639 | 10/1980 |
| GB | 995660 | 6/1965 |
| GB | 1028211 | 5/1966 |
| GB | 1205776 | 9/1970 |
| GB | 1227444 | 4/1971 |
| GB | 2242370 | 11/1993 |
| GB | 2313410 | 11/1997 |
| GB | 2207952 | 7/1998 |
| GB | 2384027 | 1/2002 |
| GB | 0223572.9 | 10/2002 |
| GB | 0227053.6 | 11/2002 |
| GB | 0301236.6 | 6/2003 |
| GB | 0404230.5 | 2/2004 |
| GB | 0405363.3 | 3/2004 |
| GB | 0406690.8 | 3/2004 |
| GB | 0407090.0 | 3/2004 |
| GB | 0409620.2 | 4/2004 |
| GB | 0410518.5 | 5/2004 |
| GB | 0416914.0 | 7/2004 |
| GB | 0417961.0 | 8/2004 |
| GB | 0428343.8 | 12/2004 |
| GB | 0500580.6 | 1/2005 |
| GB | 0500581.4 | 1/2005 |
| GB | 0618196.0 | 9/2006 |
| GB | 0708482.5 | 5/2007 |
| GB | 0710659.4 | 6/2007 |
| GB | 0710663.6 | 6/2007 |
| GB | 0721995.9 | 11/2007 |
| GB | 0803959.6 | 3/2008 |
| GB | 0805791.1 | 3/2008 |
| GB | 0806182.2 | 4/2008 |
| GB | 0810155.2 | 6/2008 |
| GB | 0818362.6 | 10/2008 |
| GB | 0416915.7 | 7/2009 |
| JP | 03-260405 | 11/1991 |
| JP | 2004-184000 | 6/1992 |
| JP | 10-141299 | 5/1998 |
| JP | 10-226503 | 8/1998 |
| JP | 2001-354319 | 12/2001 |
| JP | 2003-515702 | 5/2003 |
| NL | 7409053 | 1/1975 |
| RU | 2040322 | 5/1992 |
| RU | 2142580 | 12/1999 |
| RU | 2152465 | 7/2000 |
| SU | 1653853 | 6/1991 |
| WF | WO 2005/082546 | 9/2005 |
| WO | WO 89/07204 | 8/1989 |
| WO | WO 89/10184 | 11/1989 |
| WO | WO 92/20453 | 11/1992 |
| WO | WO 92/20454 | 11/1992 |
| WO | WO 94/08724 | 4/1994 |
| WO | WO97/00373 | 1/1997 |
| WO | WO 97/38757 | 10/1997 |
| WO | PCT/US98/05275 | 3/1998 |
| WO | PCT/RU97/00299 | 9/1998 |
| WO | WO 00/02653 | 1/2000 |
| WO | WO 00/71235 | 1/2000 |
| WO | WO 00/09236 | 2/2000 |
| WO | PCT/RU00/00118 | 4/2000 |
| WO | WO 00/37143 | 6/2000 |
| WO | WO 01/36105 | 5/2001 |
| WO | WO 01/76764 | 10/2001 |
| WO | WO 01/94197 | 12/2001 |
| WO | WO 03/030995 | 4/2003 |
| WO | WO 03/061769 | 7/2003 |
| WO | WO 03/072952 | 9/2003 |
| WO | WO 2004/033920 | 4/2004 |
| WO | WO 2004/038031 | 6/2004 |
| WO | WO 2004/057196 | 7/2004 |
| WO | PCT/GB2005/000708 | 2/2005 |

| | | |
|---|---|---|
| WO | PCT/GB2005/000720 | 2/2005 |
| WO | WO 2005/115555 | 12/2005 |
| WO | WO 2005/123263 | 12/2005 |
| WO | WO 2006/010949 | 2/2006 |
| WO | WO 2006/024242 | 3/2006 |
| WO | WO 2006/034590 | 4/2006 |
| WO | WO 2006/132557 | 12/2006 |
| WO | WO 2007/037752 | 4/2007 |
| WO | PCT/GB2007/003492 | 9/2007 |
| WO | WO 2008/062218 | 5/2008 |
| WO | PCT/GB2008/001883 | 6/2008 |
| WO | PCT/GB2008/051042 | 11/2008 |
| WO | PCT/US2008/012571 | 11/2008 |
| WO | WO 2008/135775 | 11/2008 |
| WO | WO 2008/135783 | 11/2008 |
| WO | WO 2009/060240 | 11/2008 |
| WO | PCT/GB2009/050626 | 6/2009 |
| WO | WO 2009/147443 | 12/2009 |
| WO | WO 2010/003090 | 1/2010 |
| WO | WO 2010/041080 | 4/2010 |
| WO | WO 2010/049815 | 5/2010 |

OTHER PUBLICATIONS

Arvidson, et al., The VINNOVA water mist research project: A description of the 500 m3 machinery space tests, SP Swedish National Testing and Research Institute, SP Fire Technology, SP Report 2003:19.

Dlugogorski, et al., Water Vapour as an Ineiting Agent, Halon Options Technical Working Conference, pp. 7-18 (May 6-8, 1997).

High pressure water mist for efficient fire protection, Engineer Live (Oct. 8, 2007).

Kim, Andrew, Overview of Recent Progress in Fire Suppression Technology, Institute for Research in Construction, NRCC-45690, Invited Keynote Lecture of the $2^{nd}$ NRIFD Symposium, Proceedings, Tokyo, Japan, Jul. 17-19, 2002, pp. 1-13.

Liu, et al., A Review of water mist fire suppression systems—fundamental studies, National Research Council Canada (2000).

Liu, et al., A Review of water mist fire suppression technology: Part II—Application studies, National Research Council Canada (Feb. 2001).

Liu, et al., Review of Three Dimensional Water Fog Techniques for Firefighting, National Research Council Canada (Dec. 2002).

Mawhinney, et al., A State-of-the-Art Review of Water Mist Fire Suppression Research and Development—1996, National Research Council Canada (Jun. 1996).

Mawhinney, et al., Report of the Committee on Water Mist Fire Suppression Systems, NFPA 750, pp. 141-147 (Nov. 2002 ROC).

Nigro, et al., Water Mist Fire Protection Solution for the Under-Roof Areas of the La Scala Theatre in Milan , 2003.

PDX® FireMist Comparative Data, Pursuit Dynamics pic (Jul. 1, 2005).

Schlosser, et al., In Situ Determination of Molecular Oxygen Concentrations in Full•Scale Fire Suppression Tests Using TDLAS, The 2nd Joint Meeting of the US Sections of the Combustion Institute, Oakland, CA (Mar. 28, 2001).

Vaari, A Study of Total Flooding Water Mist Fire Suppression System Performance using a Transient One-Zone Computer Model, Fire Technology, 37, 327-342 (2001).

Fire Suppression by Water Mist, Naval Research Laboratory, Washington, DC and Physikalisch-Chemisches Institut, Universitat Heidelberg , 2001.

Patent Abstracts of Japan, JP 03-260405, published Nov. 20, 1991.

Machine English language translation by EPO of FR 135965, Mar. 1964.

BIOMASS TREATMENT PROCESS AND SYSTEM

CROSS-REFERENCE TO RELATED APPLICATIONS

This application claims benefit under 35 U.S.C. §120 of international application no. PCT/GB2008/050210, filed Mar. 21, 2008 and international application no. PCT/GB2008/050319, filed May 2, 2008. The contents of both international applications are hereby incorporated by reference as if recited in full herein.

FIELD OF THE INVENTION

The present invention provides, inter alia, a biomass treatment process and system suitable for use in the production of biofuels, including, e.g., bioethanol. More specifically, the present invention provides a single process and system for the conversion of both starch and cellulose present in a biomass composition into alcohol.

BACKGROUND OF THE INVENTION

The conversion of biomass into biofuel has taken on great significance in recent years as consumers and producers alike recognise the environmental and sustainability issues surrounding existing fossil fuels. The bulk of existing biofuel is derived from the fermentation of sugar crops and crops having high starch content, which will hereinafter be referred to as the "first generation" process. First generation processes typically involve an initial hydration step of mixing ground starch-based feedstock with water to form a slurry. The water may be pre-heated prior to being mixed with the feedstock. The slurry may additionally be heated in a vessel in order to activate the starch, and is then heated again and mixed with a liquefaction enzyme in order to convert the starch to long chain sugars. The activation stage typically uses steam-jacketed tanks or steam sparge heating to heat the slurry to the desired temperature. At the same time, agitation mixers, slurry recirculation loops, or a combination of the two mix the slurry. However, despite the presence of the recirculation pumps these heating methods can result in regions being created in the slurry tank or vessel whose temperature is much greater than the remainder of the tank. In such processes, starch hydrated early in the process can be damaged, e.g., denatured, if it comes into contact with these high temperature regions, resulting in a lower yield. These arrangements also do not provide particularly efficient mixing, as evidenced by the heat damage problem discussed above and also poor hydration of the starch.

These first generation processes normally use separate vessels for the activation and conversion stages of the process. Transfer of the slurry from the activation vessel to the conversion stage vessel is normally accomplished using centrifugal pumps, which impart a high shear force on the slurry and cause further damage to the hydrated starch as a result.

The conversion stage may also use steam- or water-jacketed tanks, or tanks heated by sparge heaters, to raise the temperature of the slurry to the appropriate level for the optimum performance of the liquefaction enzyme. Alternatively, jet cookers are employed to heat the incoming slurry into the conversion stage vessel. Not only can the slurry suffer the same heat damage as in the activation stage, but the high temperature regions also contribute to limiting the glucose yield from the process. The excessive heat of these regions promotes Maillard reactions, where the sugar molecules are destroyed due to interaction with proteins also present in the slurry. The combination of these Maillard losses with the shear losses from the transfer pumps limits the glucose yield available. Additionally, existing liquefaction processes require a long residence time for the slurry in the conversion stage to ensure that as much starch is converted to sugar as possible. This has a negative impact on the time and cost of the production process.

Crops with a high starch content have a high value in food applications (both in human and animal feed) and their sugar yield per hectare is low when compared to the potential sugar yield from cellulose and hemi-cellulose crops due to only a small percentage of the total crop being starch. Thus, a process for the derivation of biofuel from alternative sources of biomass, such as lignocellulosic biomass composed primarily of lignin, hemi-cellulose and cellulose, is of great significance to producers because lignocellulosic biomass is an extremely abundant biomass. It includes, e.g., all trees and grasses, as well as agricultural residues such as wet and dry distiller's grains, corn fibre, corn cob and sugarcane bagasse.

The process of deriving biofuel from lignocellulosic biomass will be hereinafter referred to as a "second generation" process. The second generation process converts the lignocellulosic biomass into alcohol (e.g. ethanol) in three stages: a first pre-treatment stage to disrupt the cellular structure of the biomass, a second hydrolysis stage in which the cellulosic part of the biomass is converted to short-chain sugars, and a third fermentation stage in which these sugars are converted to alcohol.

To increase the yield of the hydrolysis, the pre-treatment step is needed to soften the biomass and disrupt its cellular structure, thereby exposing more cellulose and hemi-cellulose material. Disruptive pre-treatment processes are normally chemical or physical in nature. Current chemical pre-treatment processes rely on a catalyst to achieve the desired disruption of the cells of the biomass. This catalyst is commonly an acid or an enzyme. The acid has the disadvantage of being harmful to the environment, whilst enzymes are relatively expensive. The most common physical pre-treatment process is steam explosion, examples of which are disclosed in Neves, U.S. Pat. No. 4,425,433 issued Jan. 10, 1984 and Foody, U.S. Pat. No. 4,461,648 issued Jul. 24, 1984. In steam explosion, the biomass is heated using high pressure steam for a few minutes, before the reactions are stopped by a sudden decompression to atmospheric pressure. A disadvantage of steam explosion is that the process must be contained within a suitable process vessel, and is thus a non-continuous process. Furthermore, the sugar yields from steam explosion are comparatively low while current costs for the process are high.

In both the first and second generation processes, yeast is used to ferment the sugars. However, the yeast is temperature sensitive and the biomass must be cooled to around 30° C. before the yeast can ferment the sugars. Cooling the biomass not only increases the length of the fermentation process, but also increases energy consumption given that the fermented biomass must be re-heated downstream for distillation.

The first generation process described above is the one most commonly used in the biofuel industry at present. In order to reduce the costs of transporting the crops for processing, biofuel processing plants are typically located in close proximity to the areas in which the crops are grown, or in areas with local markets for the two products from the process (e.g. ethanol and animal feed). In an effort to reduce costs still further, the starch-based components of the crop (e.g. corn kernels) are separated from the remainder of the crop (e.g. stalks and leaves) during harvesting, so that only the starch-based components are transported to the processing plant. However, in spite of this separation during harvesting around 10% by weight of the crop transported for processing is made up of lignocellulosic material (e.g. corn husks, corn cob) in which no starch is present. Thus, there is a negligible yield from 10% of the transported crop in a first generation process, even though that 10% is being transported to the processing plant.

A solution to this problem would be to also obtain alcohol from the lignocellulosic material present using the second generation process. However, having both first and second generation processes running alongside one another in a single processing plant has a significant impact on processing costs. Firstly, the set-up costs involved in constructing a processing plant having separate processing lines for the first and second generation processes will be much larger than that for constructing a plant with only a first generation process line. Secondly, the production costs in running the various stages of the two processes alongside one another will also be greater than those associated with running only a first generation process line.

Accordingly, one object of the present invention is to overcome one or more of the aforementioned disadvantages.

SUMMARY OF THE INVENTION

According to a first aspect of the invention, there is provided a process for the treatment of biomass, comprising:
 (i) inducing a composition including biomass and a working fluid to flow into a passage of a fluid processing apparatus;
 (ii) injecting a high velocity transport fluid into the composition through a nozzle communicating with the passage of the fluid processing apparatus, whereby the transport fluid applies a shear force to the composition such that the working fluid is atomised and a vapour and droplet flow regime is formed downstream of the nozzle;
 (iii) condensing the vapour and droplet flow regime and transferring the composition to a first holding vessel; and
 (iv) holding the composition in the first holding vessel at a first predetermined temperature for a first predetermined period of time;
 (v) wherein the process also includes the steps of adding an amylase enzyme and a cellulase enzyme to the composition.

An amylase enzyme is considered to be any enzyme suitable for converting starch to sugar. A cellulase enzyme is considered to be any enzyme suitable for converting cellulose or hemi-cellulose to sugar.

The step of injecting a high velocity transport fluid into the composition through a nozzle may include generating a low pressure region formed downstream of the nozzle.

The condensing step may be initiated by the condensing of the transport fluid downstream of the low pressure region.

The step of transferring the composition to a holding vessel may include passing the composition through a temperature conditioning unit to raise the temperature of the composition to the first predetermined temperature.

The first predetermined temperature may be between 80 and 85 degrees Celsius. The first predetermined temperature may be 83 degrees Celsius.

Alternatively, the first predetermined temperature may be between 72 and 80 degrees Celsius, preferably between 76 and 78 degrees Celsius, such as, for example, 75 degrees Celsius, or 77 degrees Celsius.

The liquefaction enzyme(s), e.g., amylase and/or cellulase enzymes may be added to the composition prior to the composition being induced into the passage of the fluid processing apparatus.

The process may further comprise:
 (i) transferring the composition to a second holding vessel following the end of the first period of time; and
 (ii) holding the composition in the second holding vessel at a second predetermined temperature for a second predetermined period of time, wherein the liquefaction enzyme, e.g., an amylase enzyme, may be added to the composition prior to the composition being induced into the passage of the fluid processing apparatus, and another liquefaction enzyme, e.g., a cellulase enzyme, may be added to the composition between the end of the first period of time and the beginning of the second period of time.

Prior to transferring the composition to the second holding vessel, the process may further comprise the step of cooling the composition to the second predetermined temperature.

The first predetermined temperature may be between 80 and 85 degrees Celsius. Preferably, the first predetermined temperature may be 83 degrees Celsius.

The second predetermined temperature may be between 50 and 60 degrees Celsius. Preferably, the second predetermined temperature may be 55 degrees Celsius.

Prior to transferring the composition to the second holding vessel, the process may further comprise:
 (i) inducing the composition into the passage of a second fluid processing apparatus; and
 (ii) injecting a high velocity transport fluid into the composition through a nozzle communicating with the passage of the second fluid processing apparatus, whereby the transport fluid applies a shear force to the composition such that the working fluid is atomised for a second time and a second vapour and droplet flow regime is formed downstream of the nozzle, wherein the cellulase enzyme is added to the composition prior to the composition being induced into the passage of the first fluid processing apparatus, and a liquefaction enzyme, e.g., an amylase enzyme, is added to the composition prior to the composition being induced into the passage of the second fluid processing apparatus.

The first predetermined temperature may be between 50 and 60 degrees Celsius. Preferably, the first predetermined temperature may be 55 degrees Celsius.

The second predetermined temperature may be between 80 and 85 degrees Celsius. Preferably, the second predetermined temperature may be 83 degrees Celsius.

The process may further comprise the steps of:
 (i) cooling the composition to a predetermined fermentation temperature;
 (ii) adding one or more fermentation agents to the composition; transferring the composition to a fermentation vessel; and
 (iii) holding the composition in the fermentation vessel at the predetermined fermentation temperature for a predetermined fermentation time.

The cooling step may comprise passing the composition through a cooling vessel. The cooling vessel may be a mash cooler.

The fermentation temperature may be between 30 and 40 degrees Celsius. Preferably, the fermentation temperature may be 35 degrees Celsius.

In the present invention, one or more fermentation agents may be added to the composition. As used herein, "fermentation agents" include well know agents used to facilitate fermentation processes and include, but are not limited to, gluco-amylase and yeast.

The process may further comprise the step of distilling the fermented composition to draw off the alcohol from the remainder of the composition.

The process may further comprise the step of:
(i) returning the recovered water or condensate to the composition flowing into the passage of the first fluid processing apparatus.

The process may further comprise the steps of:
(i) transferring the remainder of the composition to a separator; and
(ii) separating solids from the remainder of the composition.

The process may further comprise the steps of:
(i) recovering water content from the separator; and
(ii) returning the water content to the composition flowing into the passage of the first fluid processing apparatus.

The process may further comprise the steps of:
(i) inducing a portion of the composition to flow into a passage of a second fluid processing apparatus;
(ii) injecting a high velocity transport fluid into the composition through a nozzle communicating with the passage of the second fluid processing apparatus, whereby the transport fluid applies a shear force to the composition such that the working fluid is atomised and a second vapour and droplet flow regime is formed downstream of the nozzle;
(iii) condensing the second vapour and droplet flow regime and transferring the composition to a second holding vessel; and
(iv) holding the composition in the second holding vessel at a second predetermined temperature for a second predetermined period of time;
(v) wherein the first fluid processing apparatus and first holding vessel, and the second fluid processing apparatus and second holding vessel operate in parallel; and
(vi) wherein the amylase enzyme is added to the composition prior to the induction of the composition into the passage of the first fluid processing apparatus, and the cellulase enzyme is added to the portion of the composition prior to the induction of the portion of the composition into the passage of the second fluid processing apparatus.

The process may further comprise the steps of:
(i) cooling each portion of the composition to a predetermined fermentation temperature;
(ii) adding one or more fermentation agents to the composition;
(iii) transferring the portions of the composition to a fermentation vessel; and
(iv) holding the composition in the fermentation vessel at the predetermined fermentation temperature for a predetermined fermentation time.

The fermentation temperature may be between 30 and 40 degrees Celsius. Preferably, the fermentation temperature may be 35 degrees Celsius.

In this embodiment, one or more fermentation agents may be added to the composition. Preferably, two fermentation agents are added, wherein the fermentation agents are gluco-amylase and yeast.

The fermentation of the first and second portions of the composition may be carried out in a single fermentation vessel. Alternatively, the fermentation of the portions of the composition may be carried out in separate fermentation vessels.

The process may further comprise the step of distilling the fermented composition to draw off the alcohol from the remainder of the composition.

The process may further comprise the steps of:
(i) transferring the remainder of the composition to a separator; and
(ii) separating solids from the remainder of the composition.

The process may further comprise the steps of:
(i) recovering the solids content from the separator; and
(ii) returning the solids to the second portion of the composition in the passage of the second fluid processing apparatus.

The second portion of the composition may be the solids content recovered from the separator.

The transport fluid may be steam.

The working fluid may be water.

The biomass may comprise one or more starch-based crops.

According to a second aspect of the invention, there is provided a system for treatment of a composition including biomass and a working fluid, the system comprising:
(i) at least one fluid processing apparatus, the apparatus having a passage for receiving a supply of the composition, and a transport fluid nozzle having a nozzle outlet opening into the passage and having a throat portion whose cross sectional area is less than that of the outlet;
(ii) a first holding vessel in fluid communication with an outlet of the passage; and
(iii) a fermentation vessel in fluid communication with the first holding vessel.

The system may further comprise a first cooling vessel located intermediate the first holding vessel and the fermentation vessel.

The system may further comprise a second holding vessel and a second cooling vessel intermediate the first cooling vessel and the fermentation vessel.

The fluid processing apparatus may include one or more additive ports for introducing additives to the composition. An additive port may open into the passage upstream of the nozzle outlet. Alternatively, or in addition, an additive port may open into the passage immediately downstream of the nozzle outlet. The system may further comprise a further additive port adjacent the second holding vessel.

The system may further comprise a second fluid processing apparatus and a second holding vessel downstream of the first holding vessel, the second fluid processing apparatus having a second passage for receiving the composition from the first holding vessel, and a second transport fluid nozzle having a nozzle outlet opening into the second passage and having a throat portion whose cross sectional area is less than that of the outlet.

In another embodiment, the system comprises a first processing line made up of the first fluid processing apparatus and the first holding vessel, and the system further comprises a second processing line comprising:
(i) a second fluid processing apparatus, the second fluid processing apparatus having a second passage for receiving a supply of the composition, and a second transport fluid nozzle having a nozzle outlet opening into the second passage and having a throat portion whose cross sectional area is less than that of the outlet; and
(ii) a second holding vessel in fluid communication with an outlet of the second passage;

(iii) wherein the first and second processing lines are connected in parallel between a supply of the composition and the fermentation vessel.

The system may further comprise a mixing vessel in fluid communication with the inlet to the passage of the fluid processing apparatus, the mixing vessel mixing supplies of biomass and working fluid to form the composition.

The system may further comprise a pump upstream of the or each fluid processing apparatus.

The system may comprise a plurality of fluid processing apparatus connected in series and/or parallel with one another to form an array.

The system may comprise a plurality of second fluid processing apparatus connected in series and/or parallel with one another to form an array.

The system may further comprise a temperature conditioning unit for raising the temperature of the composition between the first and/or second fluid processing apparatus and its respective first and/or second holding vessel.

The system may further comprise a distillation apparatus downstream of the fermentation vessel. The system may further comprise a distillation apparatus downstream of the inlet of the mixing vessel. The system may further comprise a first return line connecting the distillation apparatus to the inlet of the fluid processing apparatus.

The system may further comprise a separation apparatus downstream of the distillation apparatus. The system may further comprise a separation apparatus downstream of the inlet of the mixing vessel. The system may further comprise a second return line which connects the separator to the inlet of the fluid processing apparatus.

The separation apparatus may comprise a centrifuge.

The system may further comprise a transport fluid supply unit in fluid communication with the or each transport fluid nozzle. The transport fluid supply unit may supply transport fluid to both the first and second fluid processing apparatus.

The transport fluid may be steam, and the conditioning unit may be a steam generator.

In another embodiment, the present invention provides bioethanol produced according to the any of the methods or systems disclosed herein. For example, the present invention includes a process for producing bioethanol from a biomass comprising:

(a) inducing at least a first portion of a composition comprising biomass and a working fluid to flow into a passage of a fluid processing apparatus;

(b) injecting a high velocity transport fluid into the composition through a nozzle communicating with the passage of the fluid processing apparatus, whereby the transport fluid applies a shear force to the composition such that the working fluid is atomised and a vapour and droplet flow regime is formed downstream of the nozzle;

(c) condensing the vapour and droplet flow regime;

(d) transferring the composition to a first holding vessel;

(e) holding the composition in the first holding vessel at a first predetermined temperature for a first predetermined period of time, wherein a liquefaction enzyme is added to the composition prior to or during the process;

(f) transferring the composition to a second holding vessel following the end of the first predetermined period of time;

(g) holding the composition in the second holding vessel at a second predetermined temperature for a second predetermined period of time;

(h) cooling the composition to a predetermined fermentation temperature;

(i) adding a fermentation agent to the composition;

(j) transferring the composition to a fermentation vessel; and (k) holding the composition in the fermentation vessel at the predetermined fermentation temperature for a predetermined fermentation time to generate a fermented composition, which comprises bioethanol.

BRIEF DESCRIPTION OF THE DRAWINGS

Preferred embodiments of the invention will now be described, by way of example only, with reference to the accompanying drawings, in which.

DETAILED DESCRIPTION OF THE DRAWINGS

Figure 1:
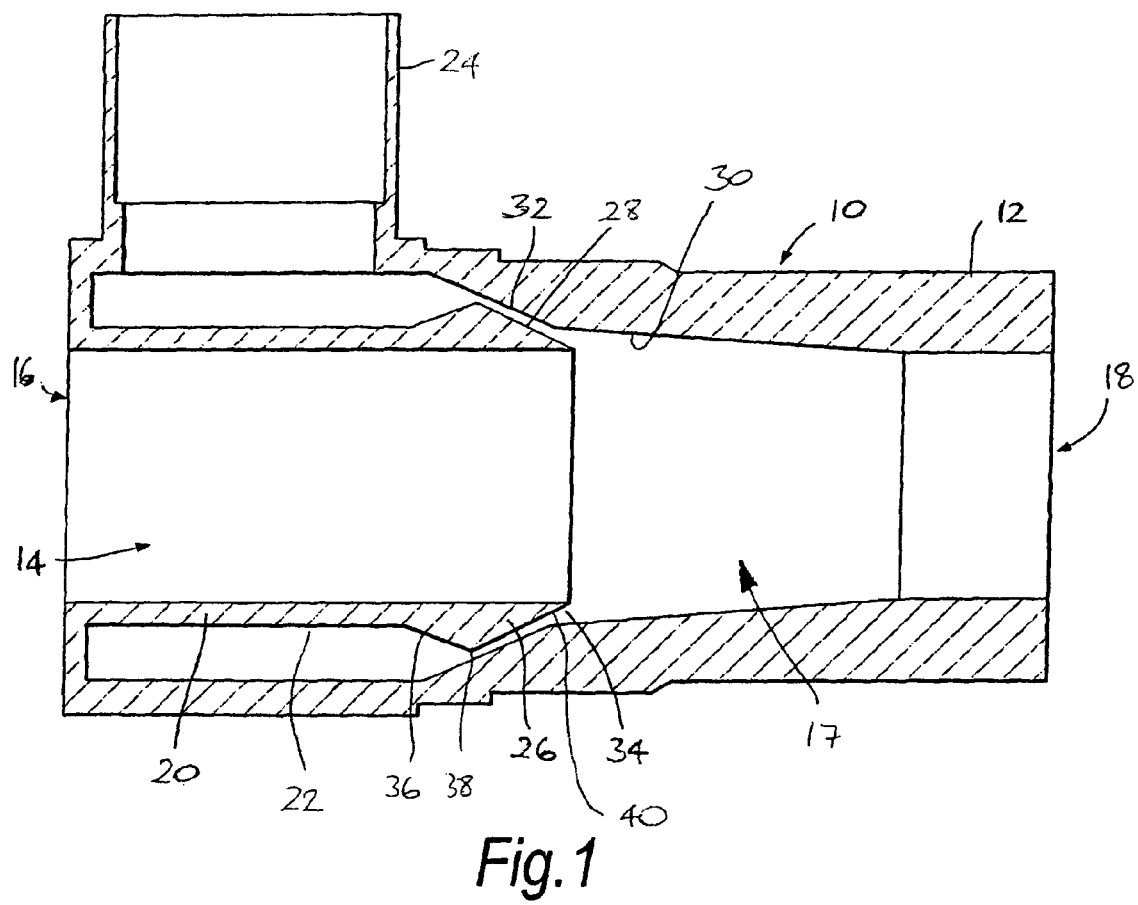
FIG. 1 is a vertical section view of a fluid processing apparatus according to the present invention.

FIG. 1 is a vertical cross section through a fluid processing apparatus, generally designated 10. The processing apparatus 10 comprises a housing 12 within which is defined a longitudinally extending passage 14. The passage has an inlet 16 and an outlet 18 and is of substantially constant circular cross section. In other words, the cross sectional area of the passage 12 is substantially constant from the inlet 16 to the outlet 18.

A protrusion 20 extends axially into the housing 12 from the inlet 16 and defines exteriorly thereof a plenum 22 for the introduction of a compressible transport fluid. The plenum 22 is provided with an inlet 24 which is connectable to a source of transport fluid (not shown in FIG. 1). The protrusion 20 defines internally thereof the inlet 16 and an upstream portion of the passage 14. The protrusion 20 has a distal end 26 remote from the inlet 16. The distal end 26 of the protrusion 20 has a thickness which increases and then reduces again so as to define an inwardly tapering surface 28. The housing 12 has a wall 30, which at a location adjacent that of the tapering surface 28 of the protrusion 20 is increasing in thickness. This increase in thickness provides a portion of the wall 30 with a surface 32 which has an inward taper corresponding to that of the tapering surface 28 of the protrusion 20. Between them the tapering surface 28 of the protrusion 20 and the tapering surface 32 of the wall 30 define an annular nozzle 34. The nozzle 34 has a nozzle inlet 36 in flow communication with the plenum 22, a nozzle outlet 40 opening into the passage 14, and a nozzle throat 38 intermediate the nozzle inlet 36 and the nozzle outlet 40. The nozzle throat 38 has a cross sectional area which is less than that of either the nozzle inlet 36 or the nozzle outlet 40. The passage 14 also includes a mixing region 17, which is located in the passage immediately downstream of the nozzle outlet 40.

Figure 2:
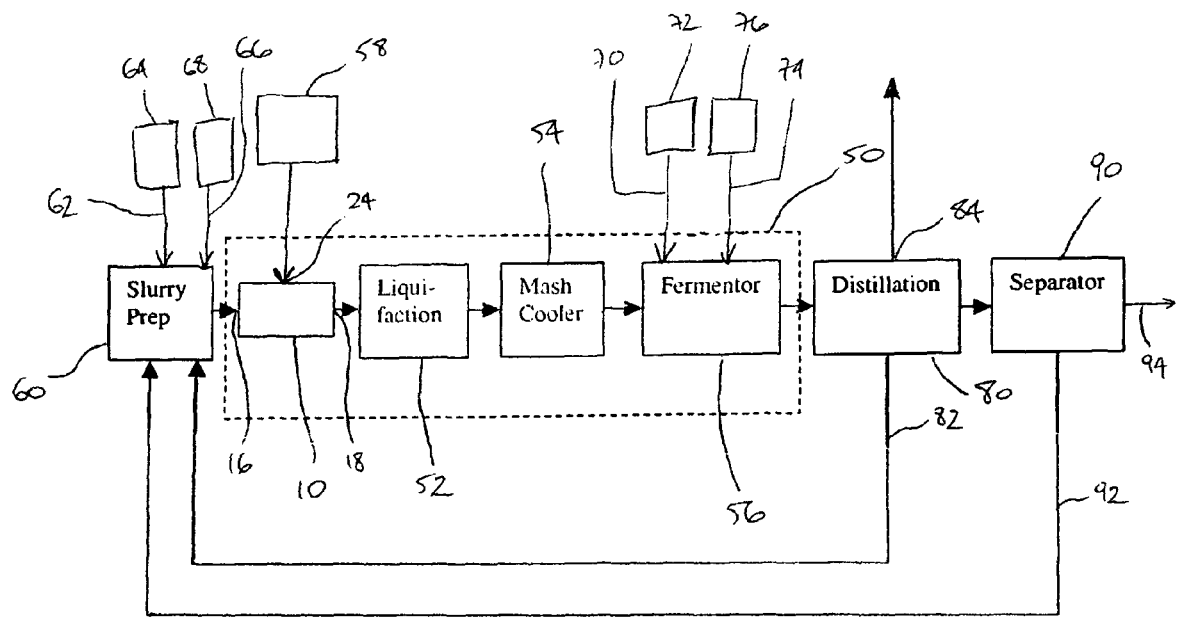
FIG. 2 is a schematic view of a first embodiment of a system for treatment of a biomass composition according to the present invention.

FIG. 2 shows a first preferred embodiment of a system for treatment of a biomass composition which incorporates a fluid processing apparatus of the type shown in FIG. 1. A biomass composition is a composition which includes biomass and a working fluid. In the embodiments described herein the preferred working fluid is water, although other fluids suitable for carrying out the process may be used. The term "biomass" is used in this specification to describe any biological material that can be used as a fuel or energy source. Non-limiting examples of suitable types of biomass include forest products, untreated wood products, energy crops and short rotation coppice, as well as animal waste, industrial and biodegradable municipal products from food processing and high energy crops such as rape, sugar cane, and maize. However, whilst not limited to this particular type of biomass, the most preferred biomass for use in the systems and processes of the present invention are starch-based crops such as corn, wheat and barley, for example. The biomass may also be provided for use in the systems and processes of the present invention in a pre-ground form.

The treatment system, generally designated 50, comprises a fluid processing apparatus 10 and a holding vessel 52 in fluid communication with the outlet 18 of the processing apparatus 10. The holding vessel 52 is preferably insulated and enclosed by a heated water jacket (not shown) and contains a motor-driven agitator (not shown) to mix and agitate the contents of the vessel 52. The system 50 also comprises a cooling vessel 54 in fluid communication with the holding vessel 52, and a fermentation vessel 56 in fluid communication with the cooling vessel 54. A transport fluid supply 58 is connected to the plenum inlet 24 of the processing apparatus 10 so that transport fluid can be supplied thereto. Although not shown, the system may also comprise a pump upstream of the fluid processing apparatus for inducing fluid into the passage 14 of the processing apparatus 10. Similarly, a temperature conditioning unit (TCU) (not shown) may be included in the system 50 between the fluid processing apparatus 10 and the holding vessel 52. The TCU comprises one or more fluid processing apparatus of the type illustrated in FIG. 1. Where there is more than one processing apparatus in the TCU, they are preferably arranged in series. The temperature conditioning unit can gently increase the temperature of any fluid passing from the fluid processing apparatus 10 to the holding vessel 52.

The system 50 enclosed within the dotted lines in FIG. 2 can be installed into an existing biomass processing line or, where necessary, additional components can be added to the system 50 to create a complete biomass processing line. In this case, the system may also comprise a mixing vessel 60 located upstream of the processing apparatus 10 and in fluid communication with the inlet 16 of the apparatus 10. The mixing vessel 60 is preferably enclosed by a heated water jacket (not shown) and has a motor-driven agitator (not shown) for mixing and agitating the contents of the vessel 60. The mixing vessel 60 also includes first and second additive lines 62, 66 which are connected to respective first and second additive supplies 64, 68. The system may also comprise third and fourth additive lines 70, 74 which are connected to the fermentation vessel 56 for the supply of fermenting agents thereto from third and fourth additive supplies 72, 76. A distillation vessel 80 may be connected in fluid communication with the fermentation vessel 56. In addition, there may be provided a holding tank (not referenced) located between the fermentation vessel 56 and the separation vessel 90. The distillation vessel 80 has an outlet 84 and may also include a return line 82 which is in fluid communication with the inlet 16 of the processing apparatus 10, either directly or via the mixing vessel 60 when present, as shown in FIG. 2. Finally, the system 50 may also comprise a separation vessel 90 connected in fluid communication with the distillation vessel 80. The separation vessel 90 preferably comprises a centrifuge and includes a second return line 92 and a drain line 94. As with the return line 82 of the distillation vessel 80, the second return line 92 is also in fluid communication with the inlet 16 of the processing apparatus 10, either directly or via the mixing vessel 60. The drain line 94 allows contents within the separator 90 to be removed or drained.

Figure 3:
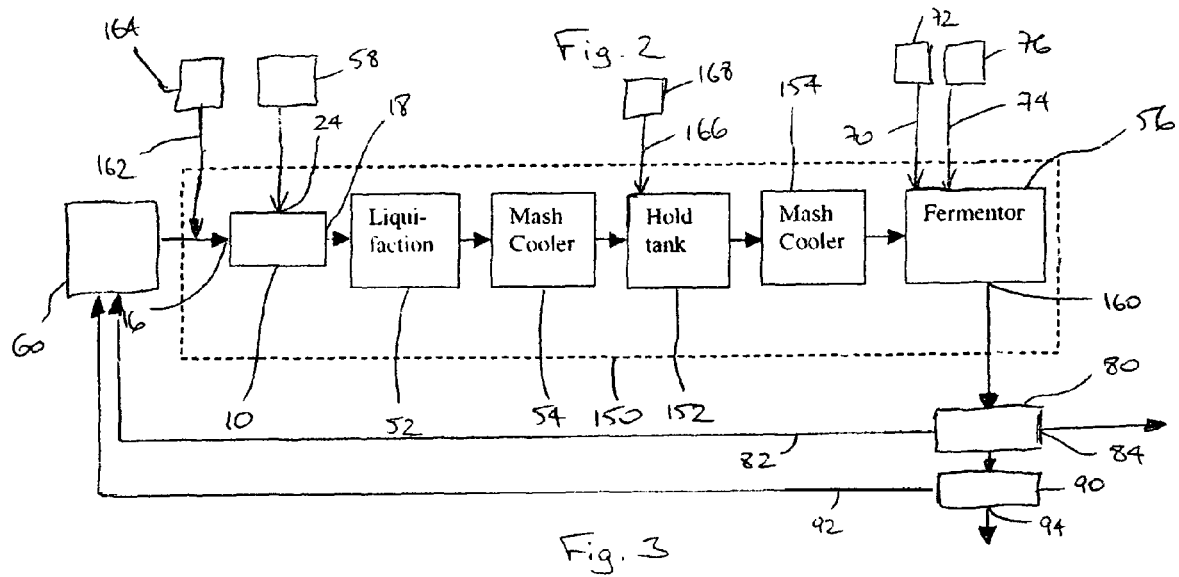
FIG. 3 is a schematic view of a second embodiment of a system for treatment of a biomass composition according to the present invention.

FIG. 3 shows a second embodiment of the system, generally designated 150. The system 150 comprises a fluid processing apparatus 10 of the type shown in FIG. 1, and a first holding vessel 52 in fluid communication with the outlet 18 of the processing apparatus 10. The system 150 also comprises a cooling vessel 54 in fluid communication with the first holding vessel 52, and a fermentation vessel 56 downstream of the cooling vessel 54. A transport fluid supply 58 is connected to the plenum inlet 24 of the processing apparatus 10 so that transport fluid can be supplied thereto. Where the second embodiment differs to the first embodiment is that the system 150 further comprises a second holding vessel 152 and a second cooling vessel 154 connected in series with the other components of the system 150 between the first cooling vessel 54 and the fermentation vessel 56. Both the first and second holding vessels 52, 152 are preferably insulated and enclosed by heated water jackets (not shown) and each contains a motor-driven agitator to mix and agitate the contents of the vessels 52, 152.

In the system 150 a first additive supply 164 is connected to the inlet 16 of the processing apparatus 10 by a first additive line 162, and the second additive supply 168 is connected by the second additive line 166 to the second holding vessel 152. The system 150 may also comprise third and fourth additive lines 70, 74 which are connected to the fermentation vessel 56 for the supply of fermenting agents thereto from third and fourth additive supplies 72, 76.

The system 150 enclosed within the dotted lines in FIG. 3 can be installed into an existing biomass processing line or, where necessary, additional components can be added to the system 150 to create a complete biomass processing line. In this case, the system may also comprise a mixing vessel 60 located upstream of the processing apparatus 10 and in fluid communication with the inlet 16 of the apparatus 10. The mixing vessel 60 is preferably enclosed by a heated water jacket (not shown) and has a motor-driven agitator (not shown) for mixing and agitating the contents of the vessel 60. When the mixing vessel 60 forms part of the system 150, the first additive line 162 may be connected to the mixing vessel 60 instead of the inlet of the fluid processing apparatus 10. A distillation vessel 80 may be connected to an outlet 160 of the fermentation vessel 56. The distillation vessel 80 has an outlet 84 and may also include a return line 82 which is in fluid communication with the inlet 16 of the processing apparatus, either directly or via the mixing vessel 60 when present, as shown in FIG. 3. Finally, the system 150 may also comprise a separation vessel 90 connected in fluid communication with the distillation vessel 80. The separation vessel 90 preferably includes a centrifuge and includes a second return line 92 and a drain line 94. As with the return line 82 of the distillation vessel 80, the second return line 92 is also in fluid communication with the inlet 16 of the processing apparatus, either directly or via the mixing vessel 60. The drain line 94 allows contents within the separator 90 to be removed or drained.

FIGS. 4-7 show other preferred embodiments of the system of the present invention. As with the first and second embodiments of the system, these additional embodiments of the system may be supplemented with the mixing, distillation and separation vessels shown in FIGS. 2 and 3, but these supplementary vessels are not illustrated or described with respect to these further embodiments for reasons of brevity.

Figure 4:
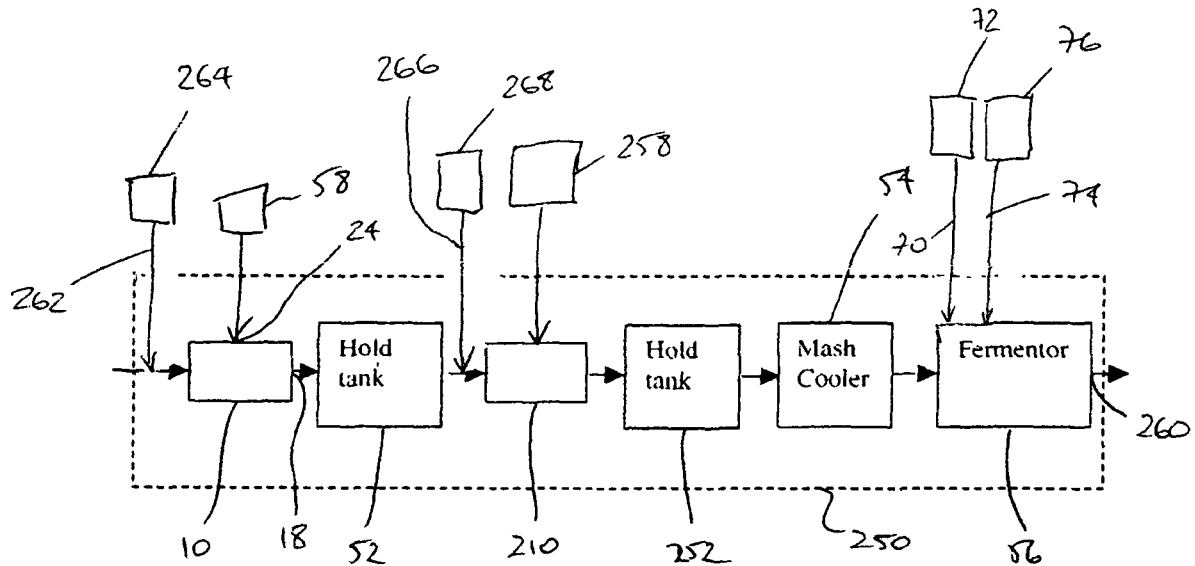
FIG. 4 is a schematic view of a third embodiment of a system for treatment of a biomass composition according to the present invention.

FIG. 4 shows a third embodiment of the system of the present invention, generally designated 250. The system 250 comprises a fluid processing apparatus 10 of the type shown in FIG. 1, and a first holding vessel 52 in fluid communication with the outlet 18 of the processing apparatus 10. The system 250 also comprises a cooling vessel 54 in fluid communication a fermentation vessel 56, both of which are downstream of the first holding vessel 52. A transport fluid supply 58 is connected to the plenum inlet 24 of the processing apparatus 10 so that transport fluid can be supplied thereto. Where the third embodiment differs to the preceding embodiments is that the system 250 further comprises a second fluid processing apparatus 210 and a second holding vessel 252 connected in series with the other components of the system 250 between the first holding vessel 52 and the cooling vessel 54. The second processing apparatus 210 is substantially identical to the first processing apparatus 10 illustrated in FIG. 1, and has a second transport fluid supply 258 connected to its respective plenum inlet.

In the system 250 a first additive supply 264 is connected to the inlet 16 of the first processing apparatus 10 by a first additive line 262, whilst the second additive supply 268 is connected by a second additive line 266 to the inlet of the second processing apparatus 210. The system 250 may also comprise third and fourth additive lines 70, 74 which are connected to the fermentation vessel 56 for the supply of fermenting agents thereto from third and fourth additive supplies 72, 76. The fermentation vessel 56 has an outlet 260.

Figure 5:
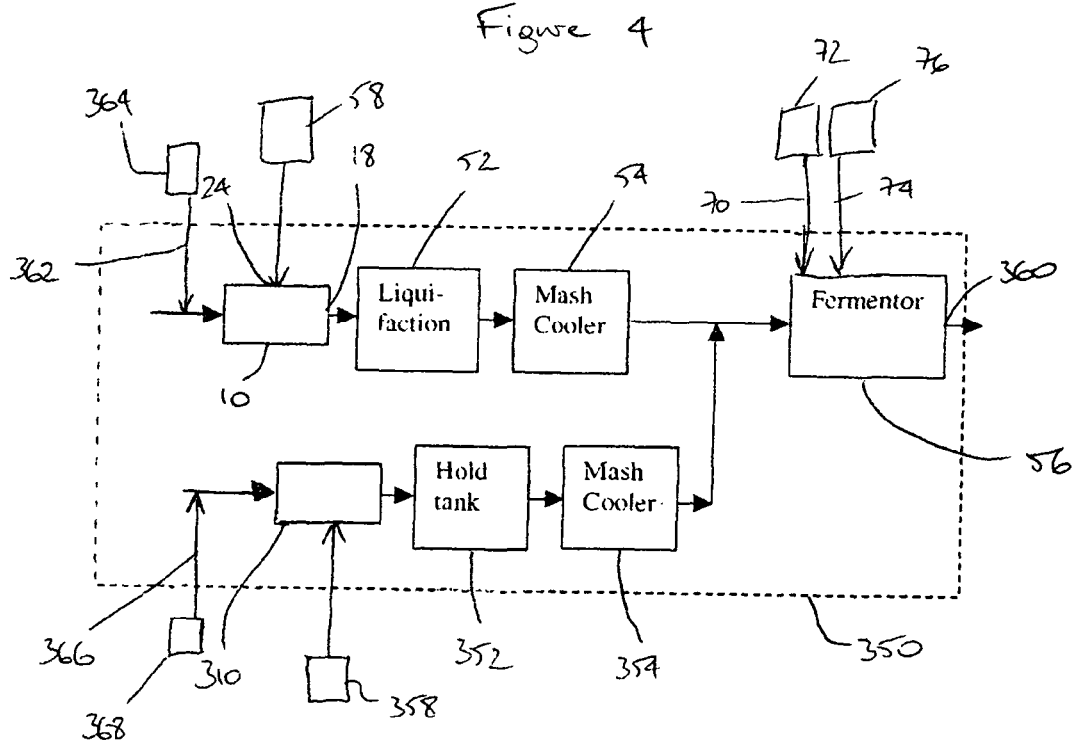
FIG. 5 is a schematic view of a fourth embodiment of a system for treatment of a biomass composition according to the present invention.

FIG. 5 shows a fourth embodiment of the system of the present invention, generally designated 350. The system 350 comprises first and second processing lines which are in parallel with one another and connected to a shared fermentation vessel 56 located downstream. The first processing line comprises a first fluid processing apparatus 10 of the type shown in FIG. 1, a first holding vessel 52 in fluid communication with the outlet 18 of the first processing apparatus 10, and a first cooling vessel 54 in fluid communication with the first holding vessel 52. A first transport fluid supply 58 is connected to the plenum inlet 24 of the first processing apparatus 10 so that transport fluid can be supplied thereto. The second processing line comprises a second fluid processing apparatus 310 also of the type shown in FIG. 1, a second holding vessel 352 in fluid communication with the outlet of the second processing apparatus 310, and a second cooling vessel 354 in fluid communication with the second holding vessel 352. The system 350 may include a second transport fluid supply 358 for supplying transport fluid to the plenum inlet of the second processing apparatus 310.

Both the first and second cooling vessels 54, 354 are in fluid communication with the fermentation vessel 56 located downstream.

In the system 350 a first additive supply 364 is connected to the inlet 16 of the first processing apparatus 10 by a first additive line 362, whilst the second additive supply 368 is connected by a second additive line 366 to the inlet of the second processing apparatus 310. The system 350 may also comprise third and fourth additive lines 70, 74 which are connected to the fermentation vessel 56 for the supply of fermenting agents thereto from third and fourth additive supplies 72, 76. The fermentation vessel 56 has an outlet 360 which may connect the fermentation vessel 56 with a distillation vessel and separation vessel of the type shown in FIG. 2 in order to supplement the system. Where the distillation vessel and separation vessel are present in the system 350, the system 350 may include respective return lines (not shown) connecting the distillation and separation vessels with the inlet of the second processing apparatus 310. The system 350 may also include a mixing vessel (not shown) upstream of the first and second processing lines, or else dedicated first and second mixing vessels for each of the first and second processing lines.

Figure 6:
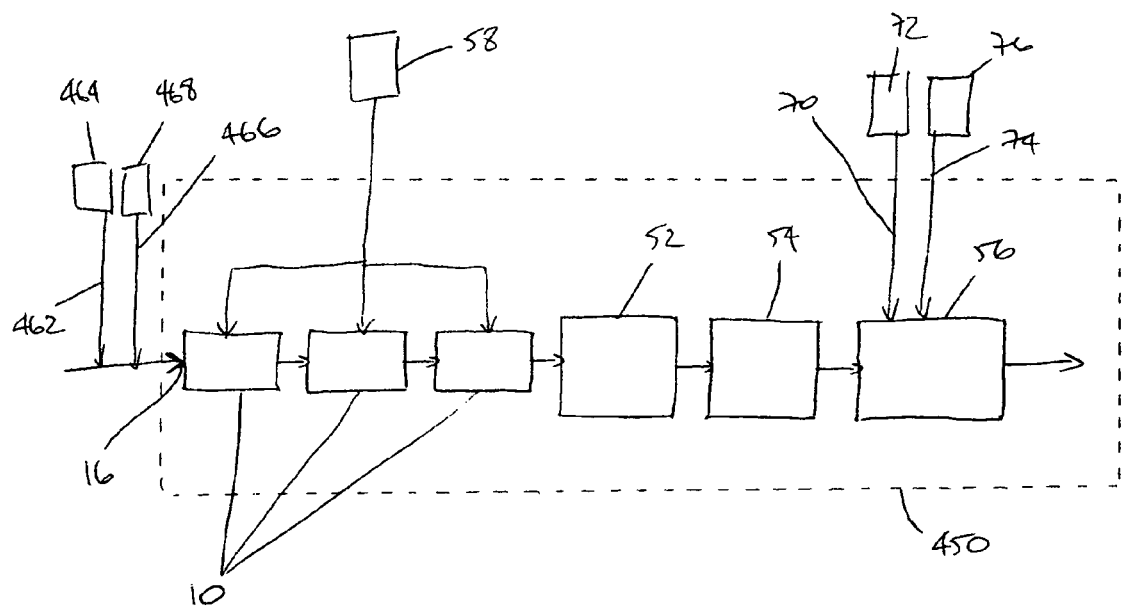
FIG. 6 is a schematic view of a fifth embodiment of a system for treatment of a biomass composition according to the present invention.
Figure 7:
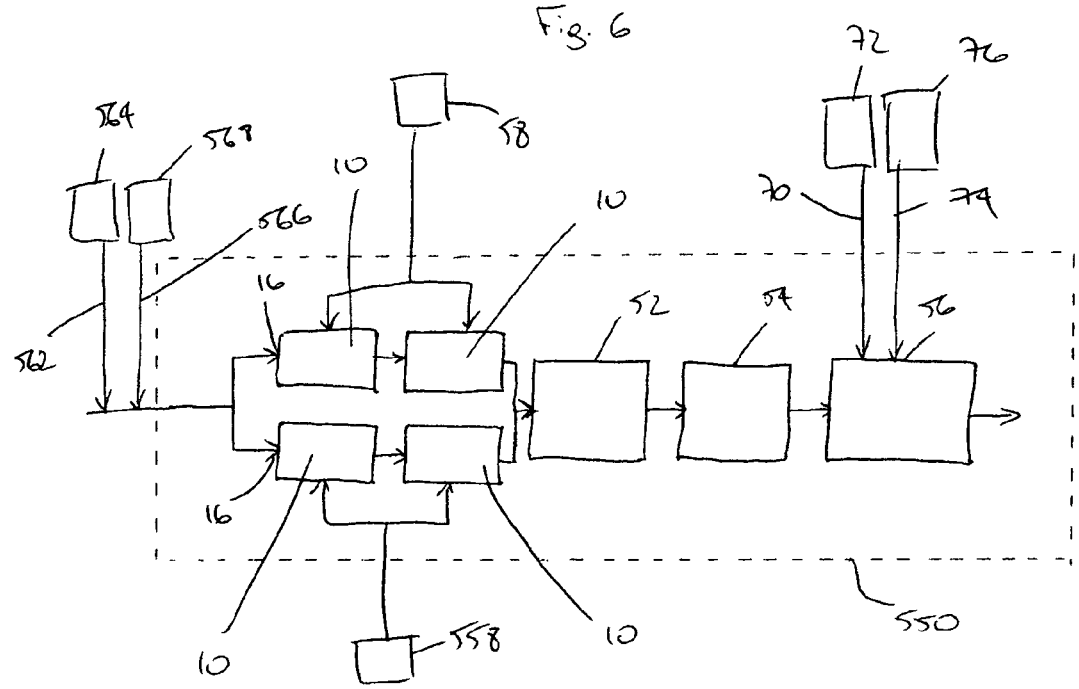
FIG. 7 is a schematic view of a sixth embodiment of a system for treatment of a biomass composition according to the present invention.

FIGS. 6 and 7 show fifth and sixth embodiments of a system in accordance with the present invention. The systems, generally designated 450 and 550, are similar to the system 50 shown in FIG. 2. They each have a holding vessel 52, a cooling vessel 54 in fluid communication with the holding vessel 52, and a fermentation vessel 56 in fluid communication with the cooling vessel 54. Where the systems 450, 550 differ from the systems of the preceding embodiments is in respect of the fluid processing apparatus. Instead of a single fluid processing apparatus upstream of the holding vessel 52, each system 450, 550 utilizes an array of fluid processing apparatus.

In the system 450 of the fifth embodiment, an array of fluid processing apparatus 10 is provided in which the apparatus 10 are arranged in series with one another upstream of the holding vessel 52. The array of processing apparatus may share a single transport fluid supply 58, as illustrated in FIG. 6, or else each processing apparatus may have its own dedicated transport fluid supply. The system 450 may include first and second additive lines 462, 466 which connect respective first and second additive supplies 464, 468 to the inlet 16 of the first fluid processing apparatus 10 in the array. As with the preceding embodiments, third and fourth additive lines 70, 74 may be present in the system 450 to connect respective third and fourth additive supplies 72, 76 to the fermentation vessel 56.

In the system 550 of the sixth embodiment, an array of fluid processing apparatus 10 is provided in which first and second pairs of the apparatus 10 are arranged in parallel upstream of the holding vessel 52. The array of processing apparatus may share a single transport fluid supply, or else each pair of processing apparatus may have a respective first and second transport fluid supply 58, 558, as shown in FIG. 7. Equally, each individual apparatus 10 may have its own dedicated supply of transport fluid. The system 550 may include first and second additive lines 562, 566 which connect respective first and second additive supplies 564, 568 to the inlets 16 of the first fluid processing apparatus 10 in each pair forming the array. As with the preceding embodiments, third and fourth additive lines 70, 74 may be present in the system 450 to connect respective third and fourth additive supplies 72, 76 to the fermentation vessel 56.

Preferred embodiments of a process for the treatment of a composition including biomass and a working fluid will now be described, with reference to the accompanying drawings.

A first embodiment of the process utilizes the first embodiment of the system 50 illustrated in FIG. 2. The composition to be treated includes a mixture of biomass and a working fluid. As stated above, the biomass may be obtained from a wide variety of sources but it is preferred that the biomass is a starch-based crop (e.g. corn). As also stated above, the working fluid is preferably water. The biomass and working fluid may be mixed together to form the composition at a location remote from the system 50. Alternatively, if the system 50 includes the mixing vessel 60, the composition can be formed in the mixing vessel 60. The ground starch-based crop is introduced into the working fluid in the mixing vessel 60 at a controlled mass addition flow rate. The introduction of the crop may be done manually or automatically, and may be introduced continuously or as a batch. The mixing of the crop and working fluid leads to the composition forming a slurry. Separately, an amylase enzyme and a cellulase enzyme held in the first and second additive supplies 64, 68 are also added to the composition via the respective first and second additive supply lines 62, 66. Preferably, the ratio of crop to liquid content in the slurry is 20-40% by weight. Optionally, one or more PH adjusters (e.g. dilute sulphuric acid, ammonia) and/or a surfactant can also be added to the slurry at this point.

The amylase enzyme utilized in each of the embodiments of the treatment process described herein is preferably α-amylase, with an activity of between 750 and 824 AGU/g. The enzyme activity is presented per unit mass of wet crop or feedstock.

Heated water is fed into the water jacket surrounding the mixing vessel 60 and the heated water jacket then heats the slurry in the vessel 60 to a temperature of typically 30-60° C., most preferably 30-40° C., and holds the slurry at this temperature for 30-120 minutes. The motor-driven agitator stirs the slurry with gentle (i.e. low shear) agitation whilst the slurry is held in the mixing vessel 60.

The slurry is held at the desired temperature in the mixing vessel 60 for a sufficient period of time to allow the starch content to be prepared for full hydration. When the slurry has been soaked in the mixing vessel 60 for sufficient time, it is drained from the vessel 60 and induced into the passage 14 of the fluid processing apparatus 10 via the inlet 16. The composition may be induced into the fluid processing apparatus 10 under gravity. Alternatively, if a pump is present, the pump can induce the composition into the fluid processing apparatus 10 under low shear conditions.

Referring to FIG. 1, when the slurry reaches the fluid processing apparatus 10, slurry will pass into the passage 14 through inlet 16 and out of the outlet 18. A transport fluid, which in this non-limiting example is preferably steam, is fed from the transport fluid supply 58 at a preferred pressure of between 5-7 Bar to the plenum inlet 24. Introduction of the transport fluid through the inlet 24 and plenum 22 causes a jet of steam to issue from the nozzle outlet 40 at a very high, preferably supersonic, velocity. As the steam is injected into the slurry, a momentum and mass transfer occurs between the two which results in the atomization of the working fluid component of the slurry to form a vapour and droplet flow regime. In other words, the working fluid within the composition is broken down into very small droplets which are dispersed in a continuous vapour phase. This transfer is enhanced through turbulence generated in the mixing region 17 of the passage 14 by the expansion of the steam as it exits the nozzle 34. The steam injected into the mixing region 17 applies a shearing force to the slurry which not only atomizes the working fluid component but also disrupts the cellular structure of the ground crop suspended in the slurry. This disruption of the cellular structure separates any starch granules present from the crop whilst at the same time exposing as much of the lignocellulosic material also present in the composition as possible.

Figure 8:
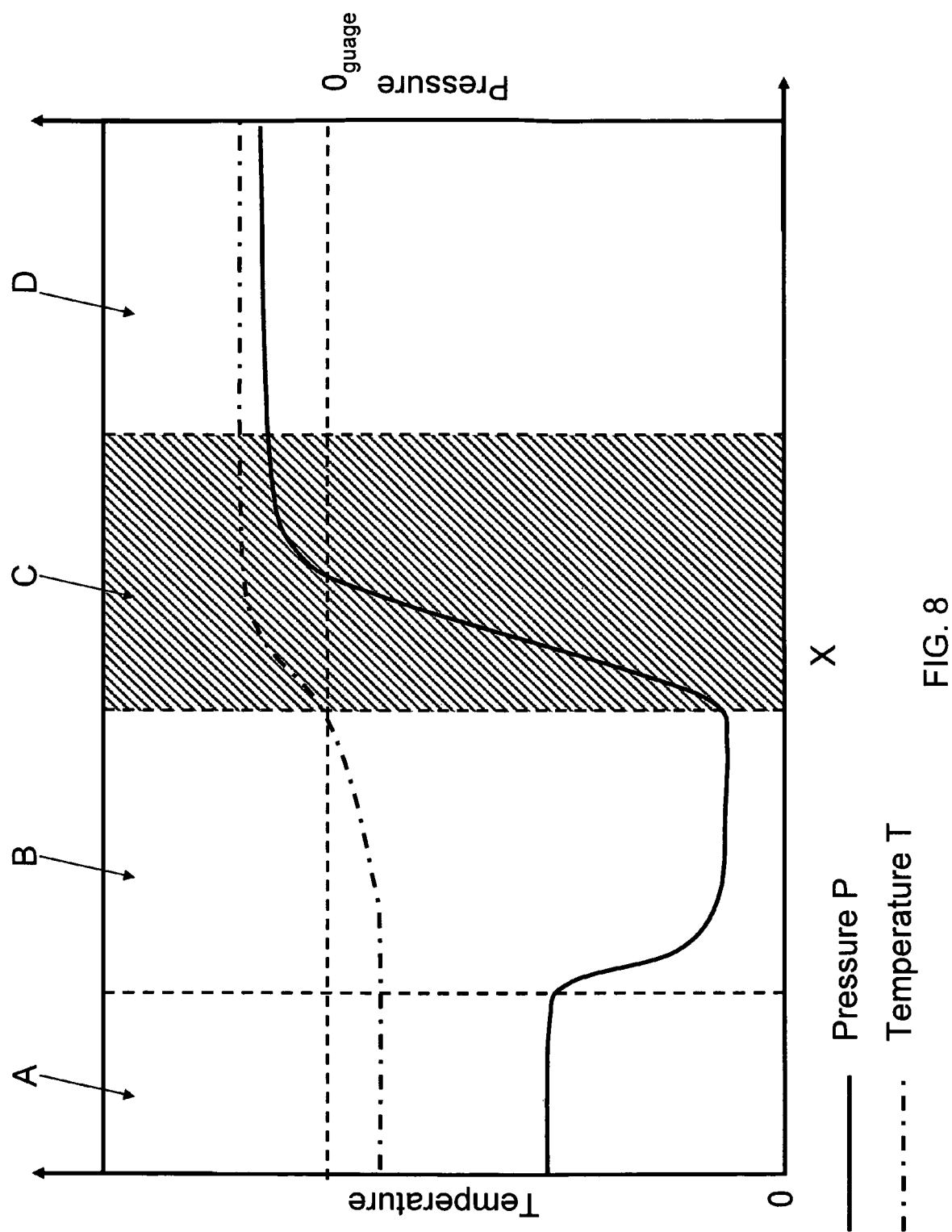
FIG. 8 is a graph showing variations in pressure and temperature of a biomass composition as it passes through the fluid processing apparatus shown in FIG. 1.

The temperature and pressure of the composition as it passes through the fluid processing apparatus 10 can be seen in the graph of FIG. 8, which shows the profile of the temperature and pressure as the composition passes through various points in the apparatus 10 of FIG. 1. The graph has been divided into four sections A-D, which correspond to various sections of the apparatus 10. Section A corresponds to the section of the passage 14 between the inlet 16 and the nozzle 34. Section B corresponds to the upstream section of the mixing region 17 extending between the nozzle 34 and an intermediate portion of the mixing region 17. Section C corresponds to a downstream section of the mixing region 17 extending between the aforementioned intermediate portion of the mixing region 17 and the outlet 18, while section D illustrates the temperature and pressure of the composition as it passes through the outlet 18.

The steam is injected into the composition at the beginning of section B of the FIG. 8 graph. The injection of the steam, preferably at a supersonic velocity, and its expansion upon exiting the nozzle 34, generates a low pressure area in the section of the mixing region 17 immediately downstream of the nozzle 34. At a point determined by the steam and geometric conditions, and the rate of heat and mass transfer, the velocity of the steam will reduce and the steam will begin to condense. The steam condensation may continue and form a condensation shock wave in the downstream section of the mixing region 17. The forming of a condensation shock wave causes a rapid increase in pressure of the composition, as can be seen in section C of FIG. 8, and the composition condenses back into a liquid phase in section D of FIG. 8.

As explained above, as the steam is injected into the composition through nozzle 34 a pressure reduction may occur in the upstream section of the mixing region 17. This reduction in pressure forms an at least partial vacuum in this upstream section of the mixing region 17 adjacent the nozzle outlet 40. Tests have revealed that an approximately 90% vacuum can be achieved in the region 17 as the steam is injected.

As previously stated, the shear force applied to the composition by the injected steam and the subsequent turbulent flow created disrupts the cellular structure of the ground crop suspended in the slurry. As the slurry passes through the partial vacuum and condensation shock wave formed in the mixing region 17, it is further disrupted by the changes in pressure occurring, as illustrated by the pressure profile in sections B and C of FIG. 8.

As the starch granules are separated from the crop in the apparatus 10, the granules are almost instantaneously further hydrated, heated and activated due to the introduction of the steam. The apparatus 10 simultaneously pumps and heats the composition to complete the hydration and activate or gelatinize the starch content as the slurry passes through. In other words, homogenous swelling of the starch granules will occur due to the granules absorbing water in the presence of heat. This causes the hydrogen bonding between the starch polymers within the granule to loosen, and there is an irreversible breakdown of the crystalline structure inside the granules.

In addition, the apparatus mixes the amylase and cellulase enzymes into the composition, providing a homogenous distribution and high level of contact with the starch and lignocellulosic material in the liquid phase. The temperature of the composition as it leaves the apparatus 10 is preferably between 74-76° C.

The temperature at which the composition leaves the apparatus 10 is selected to avoid any heat damage to the composition during the activation of the starch content and disruption of the cells. However, this temperature may be below the temperature for optimal performance of the amylase and cellulase enzymes. The temperature of the composition may therefore need to be raised without subjecting the composition to excessively high temperatures or additional shear forces. This gentle heating may be achieved using the optional temperature conditioning unit (TCU) located between the apparatus 10 and the holding vessel 52.

As described above, the TCU comprises one or more fluid processing apparatus of the type illustrated in FIG. 1. The pressure of the steam supplied to the apparatus making up the TCU is controlled so that it is comparatively low when compared to that of the steam supplied to the fluid processing apparatus 10 upstream of the TCU. A preferred steam input pressure for the apparatus of the TCU is between 0.5-2.0 Bar. Consequently, the transport fluid velocity is much lower so little or no shear force or condensation shock is applied to the composition by the injected steam as the composition passes through the TCU. Instead, the TCU merely uses the low pressure steam to gently raise the temperature of the composition.

Once it has passed through the TCU, the composition is preferably at a temperature of between 80-85° C., and most preferably 83° C. The composition then flows downstream into the holding vessel 52. The water jacket of the holding vessel 52 receives heated water which maintains the slurry at the aforementioned temperature. If no TCU is present in the system 50, the heated water jacket is used to increase the temperature of the slurry to within the desired range and then maintain it. The composition is held in the holding vessel 52 for a sufficient residence time to allow the amylase and cellulase enzymes to convert the starch, cellulose and hemicellulose present into sugars. At the end of the residence time, the composition is transferred to the fermentation vessel 56. Thus, the methods and systems of the present invention may be used to generate polysaccharides from a biomass, which may, if desired, be further processed into alcohol, such as ethanol, particularly bioethanol.

The preferred temperature of the composition for fermentation is between 30 and 40° C., and most preferably 35° C. To reduce the temperature of the composition between the holding vessel 52 and the fermentation vessel 56, the composition can be passed through the cooling vessel 54, which operates in the same manner as a conventional mash cooler. Alternatively, if the cooling vessel 54 is not present the composition can be left to cool to the desired temperature in the fermentation vessel 56.

Fermentation agents are preferably added to the composition either in the fermentation vessel 56 or immediately upstream thereof. The agents are contained in the third and fourth additive supplies 72, 76 and delivered into the composition via the respective additive lines 70, 74. The fermentation agents used may be gluco-amylase and yeast. Once the agents have been added and the composition is within the desired temperature range, the composition is held in the fermentation vessel within the desired temperature range for a sufficient time to allow the agents to convert the sugars present into alcohol, such as, e.g., bioethanol.

Once the fermentation stage has been completed, the composition can be transferred for subsequent distillation and separation. As previously stated, these subsequent processes may or may not be part of the system and process of the present invention. In the distillation vessel 80, the composition is boiled and any alcohol (ethanol) present in the composition evaporates and is drawn off via the outlet 84. Molecular sieves may be provided downstream of the outlet to remove any remaining impurities in the alcohol. Additionally, there may be provided a water recovery system (not shown) located between the distillation vessel 80 and the separator vessel 90. The remainder of the composition which is left in the distillation vessel 80 is known as "whole stillage". This whole stillage is made up of two main constituents: the non-starch elements of the ground crop (also known as "distiller's grains") and water (also known as "thin stillage"). This whole stillage is transferred from the distillation vessel 80 into the separation vessel 90 so that the distiller's grains and thin stillage can be separated from one another. The separation is preferably achieved using a centrifuge. The separated thin stillage can be added back into the composition via the return line 92 if desired. The distiller's grains can be processed and used as animal feed.

The process employed by the second embodiment of the system 150, as shown in FIG. 3, is similar to that employed by the first embodiment of the system 50. The composition to be treated includes a mixture of biomass and a working fluid. The biomass is preferably is a starch-based crop (e.g. corn) and the working fluid is preferably water. The biomass and working fluid may be mixed together to form the composition at a location remote from the system 150. Alternatively, if the system 150 includes the mixing vessel 60, the composition can be formed in the mixing vessel 60. The ground starch-based crop is introduced into the working fluid in the mixing vessel 60 at a controlled mass addition flow rate. The mixing of the crop and working fluid leads to the composition forming a slurry. Separately, an amylase enzyme held in the first additive supply 164 is also added to the composition via the first additive supply line 162. The first additive line 162 can supply the amylase enzyme direct to the mixing vessel 60, when present, or else to the inlet 16 of the fluid processing apparatus 10. Preferably, the percentage of crop to liquid content in the slurry is 20-40% by weight. Optionally, one or more PH adjusters and/or a surfactant can also be added to the slurry at this point.

Heated water is fed into the water jacket surrounding the mixing vessel 60 and the heated water jacket then heats the slurry in the vessel 60 to a temperature of typically 30-60° C., most preferably 30-40° C., and holds the slurry at this temperature for 30-120 minutes. The motor-driven agitator stirs the slurry with gentle (i.e. low shear) agitation whilst the slurry is held in the mixing vessel 60.

The slurry is held at the desired temperature in the mixing vessel 60 for a sufficient period of time to allow the starch content to be prepared for full hydration. When the slurry has been soaked in the mixing vessel 60 for sufficient time, it is drained from the vessel 60 and induced into the passage 14 of the fluid processing apparatus 10 via the inlet 16. The composition may be induced into the fluid processing apparatus 10 under gravity. Alternatively, if a pump is present, the pump can induce the composition into the fluid processing apparatus 10. In such a case a low-shear pump is used. The fluid processing apparatus 10 is identical to that used in the first embodiment of the process. The manner of operation of the apparatus 10, the mechanisms taking place therein, and the resultant effects on the composition are as in the first embodiment of the process, as described above with reference to FIGS. 1 and 8. They will therefore not be described in detail again here.

As the starch granules are separated from the crop in the apparatus 10, the granules are almost instantaneously further hydrated, heated and activated due to the introduction of the steam. The apparatus 10 simultaneously pumps and heats the composition to complete the hydration and activate or gelatinize the starch content as the slurry passes through. In addition, the apparatus mixes the amylase enzyme into the composition, providing a homogenous distribution and high level of contact with the starch material in the liquid phase. The temperature of the composition as it leaves the apparatus 10 is preferably between 74-76° C.

As with the first embodiment of the process, a temperature conditioning unit (TCU) of the type described above may be included in the system 150 in order to gently raise the temperature of the composition in the same manner as described above. Once it has passed through the TCU, the composition is preferably at a temperature of between 80-85° C., and most preferably 83° C. The composition is then transferred to the first holding vessel 52. The water jacket of the first holding vessel 52 receives heated water which maintains the slurry at the aforementioned temperature. If no TCU is present in the system 150, the heated water jacket is used to increase the temperature of the slurry to within the desired range and then maintain it. The composition is held in the first holding vessel 52 for a first residence time sufficient to allow the amylase enzyme to convert the starch present in the composition into sugars. At the end of the first residence time, the composition is transferred to the second holding vessel 152.

The preferred temperature of the composition when it passes to the second holding vessel 152 is between 50 and 60° C., and most preferably 55° C. To reduce the temperature of the composition between the first and second holding vessels 52, 152, the composition can be passed through the cooling vessel 54, which operates in the same manner as a conventional mash cooler. Alternatively, if the cooling vessel 54 is not present the composition can be left to cool to the desired temperature in the second holding vessel 152. The heated water jacket of the second holding vessel 152 maintains the temperature of the composition within the desired range. A cellulase enzyme is added to the composition in the second holding vessel 152 via the second additive supply 168 and associated supply line 166. The cellulase enzyme is added in order to react with the cellulose and hemicellulose—present in the lignocellulosic material exposed when the composition passed through the fluid processing apparatus 10. The composition is held in the second holding vessel 152 for a second residence time sufficient to allow the cellulase enzyme to convert all of the cellulose and hemi-cellulose present into sugars. At the end of the second residence time, the composition is transferred to the fermentation vessel 56.

The preferred temperature of the composition for fermentation is between 30 and 40° C., and most preferably 35° C. To reduce the temperature of the composition between the second holding vessel 152 and the fermentation vessel 56, the composition can be passed through the second cooling vessel 154, which operates in the same manner as a conventional mash cooler. Alternatively, if the second cooling vessel 154 is not present the composition can be left to cool to the desired temperature in the fermentation vessel 56.

Fermentation agents are preferably added to the composition either in the fermentation vessel 56 or immediately upstream thereof. The agents are contained in the third and fourth additive supplies 72, 76 and delivered into the composition via the respective additive lines 70, 74. The fermentation agents used may be gluco-amylase and yeast. Once the agents have been added and the composition is within the desired temperature range, the composition is held in the fermentation vessel within the desired temperature range for a fermentation time sufficient to allow the agents to convert the sugars present into alcohol.

Once the fermentation stage has been completed, the composition can be transferred for subsequent distillation and separation. In the distillation vessel 80, the composition is boiled and any alcohol, such as, e.g., ethanol, present in the composition evaporates and is drawn off via the outlet 84. Molecular sieves may be provided downstream of the outlet to remove any remaining impurities in the alcohol. Additionally, there may be provided a water recovery system (not shown) located between the distillation vessel 80 and the separator vessel 90. The remainder of the composition which is left in the distillation vessel 80 is known as "whole stillage". This whole stillage is made up of two main constituents: the non-starch elements of the ground crop (also known as "distiller's grains") and water (also known as "thin stillage").

This whole stillage is transferred from the distillation vessel 80 into the separation vessel 90 so that the distiller's grains and thin stillage can be separated from one another. The separation is preferably achieved using a centrifuge. The separated thin stillage can be added back into the composition via the return line 92 if desired. The distiller's grains can be processed and used as animal feed.

The process employed by the third embodiment of the system 250, as shown in FIG. 4, has similarities with those employed by the first and second embodiments of the system 50, 150. The composition to be treated is formed from a mixture of biomass and a working fluid and prepared in the same manner as described above with respect to the second embodiment. However, it is a cellulase enzyme rather than an amylase enzyme which is initially added to the composition from the first additive supply 264. The composition may be induced into the first fluid processing apparatus 10 under gravity, or a pump can induce the composition into the first fluid processing apparatus 10 under low shear conditions. Both the first and second fluid processing apparatus 10, 210 employed in this process are identical to that used in the first and second embodiments described above. The manner of operation of the apparatus 10, 210, the mechanisms taking place therein, and the resultant effects on the composition are as previously described with reference to FIGS. 1 and 8. They will therefore not be described in detail again here.

The first processing apparatus 10 is used primarily to pre-treat the cellulosic material and mix in the cellulase enzyme. The first processing apparatus 10 also partially separates the starch granules from the crop and partially hydrates the starch granules. The second processing apparatus 210 is used to fully hydrate and activate the starch and mix in the starch enzyme. The apparatus mixes the cellulase enzyme into the composition, providing a homogenous distribution and high level of contact with any cellulose and hemi-cellulose that has been exposed by the disruption of lignocellulosic material by the first processing apparatus 10. The temperature of the composition as it leaves the first apparatus 10 is preferably between 50-60° C., and most preferably 55° C. It is then transferred to the first holding vessel 52.

The water jacket of the first holding vessel 52 receives heated water which maintains the slurry at the aforementioned temperature. The composition is held in the first holding vessel 52 for a first residence time sufficient to allow the cellulase enzyme to convert the cellulose and hemi-cellulose present in the composition into sugars. At the end of the first residence time, the composition is transferred to the second processing apparatus 210, at which point an amylase enzyme is added via the second additive supply 268.

As stated above, the second fluid processing apparatus 210 operates in the same manner as the first processing apparatus 10, with the same effect on the starch content of the composition. In addition, the apparatus mixes the amylase enzyme into the composition, providing a homogenous distribution and high level of contact with the starch material in the liquid phase. The temperature of the composition as it leaves the second apparatus 210 is preferably between 74-76° C. As before, a temperature conditioning unit may be present to gently raise the temperature of the composition to between 80 and 85° C. before the composition is transferred to the second holding vessel 252. The water jacket of the second holding vessel 252 receives heated water which maintains the slurry at the aforementioned temperature. If no TCU is present in the system 250, the heated water jacket is used to increase the temperature of the slurry to within the desired range and then maintain it. The composition is held in the second holding vessel 252 for a second residence time sufficient to allow the amylase enzyme to convert the starch present in the composition into sugars. At the end of the second residence time, the composition is transferred to the fermentation vessel 56.

As with the previously described embodiments, the preferred temperature of the composition for fermentation is between 30 and 40° C., and most preferably 35° C. To reduce the temperature of the composition between the second holding vessel 252 and the fermentation vessel 56, the composition can be passed through the cooling vessel 54, which operates in the same manner as a conventional mash cooler. Alternatively, if the cooling vessel 54 is not present the composition can be left to cool to the desired temperature in the fermentation vessel 56. The fermentation stage is identical to that of the preceding embodiments. Once the fermentation stage has been completed, the composition can be transferred via outlet 260 for subsequent distillation and separation stages, which may also be the same as those of the preceding embodiments.

The fourth embodiment of the process uses the system 350 shown in FIG. 5, where the conversion of the starch and cellulose content of the composition into sugars is carried out in first and second process lines running in parallel, before the composition is passed to a shared fermentation vessel 56. A biomass and working fluid composition of the type already described above has an amylase enzyme added to it via first additive supply 364. The resultant composition is introduced to the first process line and firstly to the first processing apparatus 10, whereupon it is atomised by the transport fluid in the same manner as the various fluid processing apparatus already described. Thus, the first fluid processing apparatus 10 hydrates and activates the starch content of the composition and homogenously mixes the amylase enzyme into the composition.

The temperature of the composition as it leaves the first apparatus 10 is again preferably between 74-76° C. and is therefore gently heated once out of the first apparatus, either by way of a temperature conditioning unit or by the water-jacketed first holding vessel 52, until within the desired 80-85° C. range. The composition is then held in the first holding vessel 52 for a first residence time sufficient to allow the amylase enzyme to convert the starch content of the composition into sugars. The composition is then transferred to the fermentation vessel 56 for a fermentation step of the type already described above. A cooling vessel 54 can reduce the temperature of the composition prior to fermentation, or else the composition may be left to cool in the fermentation vessel 56. Following fermentation, the composition is released via outlet 360 for subsequent distillation and separation.

Solids and distiller's grains obtained from the separation stage are then mixed with additional working fluid and/or liquid components drawn off during distillation or separation to form a further batch of the biomass composition. A cellulase enzyme is added to this composition, which is then induced into the second process line via the second processing apparatus 310. The second processing apparatus 310 operates in the same manner as those already described, with the result that passing the composition through the second processing apparatus 310 further disrupts the cellular structure of the solid material in the composition and homogenously mixes the cellulase enzyme into the composition. The composition preferably leaves the second apparatus 310 at a temperature of between 50 and 60° C. and is transferred to the second holding vessel 352. The composition is held in the second holding vessel 352 for a second residence time sufficient for the cellulase enzyme to convert the cellulose and hemi-cellulose exposed in the second apparatus 310 into sugars. The composition is then transferred for fermentation in the fermentation vessel 56, via a second cooling vessel 354 if necessary.

This embodiment of the process could be modified such that portions of the initial composition are fed to both the first and second process lines simultaneously, with the first line converting the starch content and the second line converting the cellulose and hemi-cellulose content into sugars before both portions of the composition are transferred to the fermentation vessel 56. It is therefore not essential that the second process line receives remnants of the composition after the separation stage.

The fifth and sixth embodiments of the process employed by the systems shown in FIGS. 6 and 7 are substantially the same as the first and second embodiments of the process as used by the systems of FIGS. 2 and 3. The formation of the biomass compositions, the addition of amylase and cellulase enzymes, the residence of the processed composition in one or two holding vessels, and the transfer and subsequent fermentation of the composition are the same in these fifth and sixth embodiments as those earlier embodiments. Where the fifth and sixth embodiments differ is that the single fluid processing apparatus has been replaced by an array of fluid processing apparatus. In the fifth embodiment of FIG. 6, the array is formed from a number of the processing apparatus arranged in series with one another. In the sixth embodiment of FIG. 7, the array is formed from two pairs of processing apparatus in series, where each pair is in parallel with the other. It should be appreciated that the number of fluid processing apparatuses and configurations of the same could be used in the process and system of the present invention.

The operation of each apparatus, and the mechanisms and effects created therein, are the same as already described. The use of arrays of the type shown in FIGS. 6 and 7 maximises the effects of the processing apparatus with respect to the hydration and activation of starch content, the disruption and exposure of lignocellulosic material, and the homogenous mixing of the enzymes with the composition. Use of arrays can also allow the temperature of the composition to be raised more gradually across the array than is possible with a single processing apparatus. This may be achieved by varying the supply pressure and/or density of the transport fluid delivered to each subsequent apparatus in the array to ensure that the desired rise in temperature of the composition is only achieved after the composition has passed through the final apparatus in the array.

Unless otherwise stated the cooling vessels, distillation vessels and separation vessels which may be included in the system of the present invention are conventional arrangements. They have therefore not been described in full detail in this specification.

The present invention provides a single treatment system and process for the conversion of both the starch and cellulose present in a biomass composition. In doing so the present invention maximises the alcohol obtained from the composition, including that from the cellulosic and lignocellulosic material inevitably transported to the processing plant with the collected crop. The cost in transporting this additional material is therefore substantially recouped with the present invention. By converting both the starch and cellulose content together, the present invention provides significant cost savings compared to existing systems in which distinct processes and process lines are needed to convert starch and cellulose content separately.

Further advantages are obtained with the present invention thanks to the use of a fluid processing apparatus of the type described herein. Using a processing apparatus of the type described allows the present invention to heat and activate the starch content of the composition while avoiding the creation of regions of extreme heat, which can damage the starch content. Prevention of these regions also reduces or eliminates Maillard effects caused by the reaction of proteins with the extracted starch. These reactions can prevent conversion of the starch to sugar and therefore reduce yields. Furthermore, the gentle agitation mixing and low shear pumping at a lower temperature also ensures that there are no high shear forces which may damage the starch content of the composition whilst held in one of the holding vessels or being transported between vessels. Such damage limits the ultimate glucose yield available from the feedstock.

The processing apparatus also ensures that the components of the composition are more thoroughly mixed than is possible using simple agitator paddles and/or recirculation loops alone. The atomization of the working fluid further ensures a more homogenous mixing of the composition than previously possible. This improved mixing increases the efficiency of the amylase and cellulase enzymes added to convert the starch and cellulose content to sugars.

As regards conversion of the lignocellulosic material, the shear action and condensation/pressure shock applied to the biomass component of the composition when in the processing apparatus further improves the performance of the present invention as this exposes more of this material present in the biomass. This allows virtually all the starch granules in the feedstock to be separated, thereby providing improved starch activation rates compared to conventional processes as the enzymatic activation is supplemented by the mechanical activation in the processing apparatus. This also allows the process to in particular provide a starch to sugar conversion ratio of substantially 100%. The process of the present invention therefore may only require the composition to pass once through the processing apparatus before it is ready to pass to the holding vessels for the conversion stage. Hence, yields are much improved as there is no time for loss build up during the process.

Exposing more starch also means that less of the amylase enzyme is needed to achieve a desired dextrose equivalent value of 12-18 before the composition is transferred to the fermentation processes. In addition, the condensation/pressure shock kills bacteria at a relatively low temperature, thereby reducing losses in any subsequent fermentation process.

Additionally, injecting a transport fluid such as steam into the biomass composition to atomize the working fluid and create a vapour and droplet flow regime ensures a greater degree of disruption to the cellular structure of the contents of the composition than that achieved by existing pre-treatment processes. Furthermore, as the disruption is at least partially achieved by the transport fluid injection, the invention enables a reduced amount of catalyst or additive to obtain the desired degree of disruption when compared with existing chemical pre-treatment processes. In fact, the disruption achieved by the transport fluid injection may remove the need for such pre-treatment additives entirely. The transport fluid injection of the processing apparatus ensures continual shear and turbulent forces on the composition. The process of the present invention can therefore be continuous, with no need to contain the process in a stand-alone vessel such as that required in steam explosion pre-treatment processes.

The high shear forces imparted by the high velocity transport fluid injection not only assist in the disruption of the cellular structure of the biomass, but also atomize the working fluid component of the composition to ensure intimate and homogenous heating and mixing of the composition with the enzymes. Such improved heating and mixing reduces the amount of time and quantity of enzymes required to achieve the necessary chemical reactions in the holding vessels.

It has also been discovered that the processes and systems of the present invention may also improve fermentation rates in the subsequent fermentation process. The improved hydration of the present invention also hydrates some proteins in the biomass feedstock. These hydrated proteins act as additional feedstock to the fermenting yeast, thereby improving the fermenting performance of the yeast.

Whilst one or more cooling vessels have been described as forming part of the system of the present invention, it is to be understood that these cooling vessels are preferable, rather than essential, components of the system. Whilst cooling vessels allow the temperature of the composition to be lowered between the holding vessels and the fermentation vessels, this cooling could be carried out within the holding vessels or fermentation vessels themselves. Such cooling vessels may include, for example, heat exchangers, chillers, direct injection coolers, cascade coolers, or the like.

The processing apparatus may be modified to include one or more additive ports, thereby allowing the enzymes to be added directly into the processing apparatus instead of the mixing vessel. An additive port may be provided which opens into the passage of the apparatus upstream of the nozzle outlet. Alternatively, or additionally, an additive port may be provided which opens into the passage immediately downstream of the nozzle into the mixing region of the passage.

The arrays of processing apparatus utilized in the fifth and sixth embodiments of the system may replace the individual processing apparatus shown in the other illustrated embodiments. In the embodiments of the present invention where there is more than one fluid processing apparatus present, two or more of these multiple processing apparatus may share a single transport fluid supply. Alternatively, all of the processing apparatus present in the system may share a single transport fluid supply.

Whilst the preferred embodiments of the system described above include additive lines which connect respective additive supplies to the system, these are not essential to the system and process of the present invention. Each additive may be added manually into the system at the desired location without the need for the dedicated supplies and associated supply lines.

It has already been stated that the mixing vessel is a preferred, rather than essential, component of the system of the present invention. Equally, the initial step in the treatment process of forming the composition of biomass and working fluid in the mixing vessel is not essential. If the mixing vessel is not present, the composition may be formed at a remote location and then pumped into the system of the present invention for treatment.

Where the enzymes used require it, the first embodiment of the system and process may be modified such that the temperature of the composition during its residence time in the holding vessel may be between 72 and 80° C., and preferably between 76 and 78° C.

The preferred transport fluid used in the process and system of the present invention is steam. However, alternative transport fluids may be used. An alternative hot, condensable gas such as carbon dioxide, for example, may be used instead.

It should be understood that the process of the present invention is not limited to the use of the specific α-amylase enzyme described above. Alternative amylase enzymes such as β-amylase or λ-amylase may be employed instead. Furthermore, it should also be appreciated that more than one of each type of amylase enzyme and cellulase enzyme may be added to the composition. Other enzymes, i.e., enzymes other than amylase, cellulase, or hemi-cellulase, which are capable of acting on biomass in substantially the same manner as amylase, cellulase, or hemi-cellulase are also contemplated by and within the scope of the present invention.

These and other modifications and improvements may be incorporated without departing from the scope of the invention.

What is claimed is:

1. A process for treating biomass comprising:
   (a) inducing at least a first portion of a composition comprising biomass and a working fluid to flow into a passage of a fluid processing apparatus;
   (b) injecting a high velocity transport fluid into the composition through a nozzle communicating with the passage of the fluid processing apparatus, whereby the transport fluid applies a shear force to the composition such that the working fluid is atomised and a vapour and droplet flow regime is formed downstream of the nozzle;
   (c) condensing the vapour and droplet flow regime;
   (d) transferring the composition to a first holding vessel; and
   (e) holding the composition in the first holding vessel at a first predetermined temperature for a first predetermined period of time, wherein a liquefaction enzyme is added to the composition prior to or during the process.

2. The process according to claim 1, wherein the liquefaction enzyme is selected from the group consisting of a starch-to-sugar converting enzyme, a cellulase- or hemi-cellulase-to-starch converting enzyme, and combinations thereof.

3. The process according to claim 2, wherein the starch-to-sugar converting enzyme is an amylase and the cellulase- or hemi-cellulase-to-starch converting enzyme is a cellulase or hemi-cellulase or both.

4. The process according to claim 1, wherein step (b) comprises generating a low pressure region formed downstream of the nozzle.

5. The process according to claim 1, wherein the transport fluid is a condensable gas selected from the group consisting of steam and carbon dioxide.

6. The process according to claim 1, wherein step (d) comprises passing the composition through a temperature conditioning unit to raise the temperature of the composition to the first predetermined temperature.

7. The process according to claim 1, wherein the first predetermined temperature is between 80° C. and 85° C.

8. The process according to claim 7, wherein the first predetermined temperature is 83° C.

9. The process according to claim 1, wherein the first predetermined temperature is between 72° C. and 80° C.

10. The process according to claim 9, wherein the first predetermined temperature is between 76° C. and 78° C.

11. The process according to claim 9, wherein the first predetermined temperature is 75° C. or 77° C.

12. The process according to claim 3, wherein an amylase and a cellulase enzyme are added to the composition prior to step (a).

13. The process according to claim 1 further comprising:
   (f) transferring the composition to a second holding vessel following the end of the first predetermined period of time; and
   (g) holding the composition in the second holding vessel at a second predetermined temperature for a second predetermined period of time.

14. The process according to claim 1, wherein a first liquefaction enzyme is added to the composition prior to step (a), and a second liquefaction enzyme is added to the composition between the end of the first predetermined period of time and the beginning of the second predetermined period of time.

15. The process according to claim 14, wherein the first liquefaction enzyme is an amylase and the second liquefaction enzyme is a cellulase or hemi-cellulase, or both.

16. The process according to claim 13 further comprising prior to step (f) cooling the composition to the second predetermined temperature.

17. The process according to claim 13, wherein the second predetermined temperature is between 50° C. and 60° C.

18. The process according to claim 17, wherein the second predetermined temperature is 55° C.

19. The process according to claim 13 further comprising:
   ($e_1$) prior to step (f), inducing at least the first composition into a passage of a second fluid processing apparatus; and
   ($e_2$) injecting a second high velocity transport fluid into at least a portion of the composition through a nozzle communicating with the passage of the second fluid processing apparatus, whereby the transport fluid applies a shear force to the composition such that the working fluid is atomised and a second vapour and droplet flow regime is formed downstream of the nozzle of the second fluid processing apparatus, wherein a first liquefaction enzyme is added to the composition prior to step (a), and a second liquefaction enzyme is added to the composition prior to step (e1).

20. The process according to claim 19, wherein the first predetermined temperature is between 50° C. and 60° C.

21. The process according to claim 20, wherein the first predetermined temperature is 55° C.

22. The process according to claim 19, wherein the second predetermined temperature is between 80° C. and 85° C.

23. The process according to claim 22, wherein the second predetermined temperature is 83° C.

24. The process according to claim 19 further comprising:
   (h) cooling the composition to a predetermined fermentation temperature;
   (i) adding a fermentation agent to the composition;
   (j) transferring the composition to a fermentation vessel; and
   (k) holding the composition in the fermentation vessel at the predetermined fermentation temperature for a predetermined fermentation time to generate a fermented composition.

25. The process according to claim 24, wherein step (h) comprises passing the composition through a cooling vessel.

26. The process according to claim 25, wherein the cooling vessel is a mash cooler.

27. The process according to claim 24, wherein the predetermined fermentation temperature is between 30° C. and 40° C.

28. The process according to claim 27, wherein the predetermined fermentation temperature is 35° C.

29. The process according to claim 24, wherein the fermentation agent is selected from the group consisting of a glucoamylase, a yeast, and combinations thereof.

30. The process according to claim 24 further comprising (I) distilling the fermented composition to draw off the alcohol from the remainder of the composition.

31. The process according to claim 30 further comprising (m) returning any recovered water or condensate to the composition flowing into the passage of the first fluid processing apparatus.

32. The process according to claim 31 further comprising:
(n) transferring any remaining composition to a separator; and
(o) separating solids from the remaining composition.

33. The process according to claim 32 further comprising:
(p) recovering water content from the separator; and
(q) returning the water content to the composition flowing into the passage of the first fluid processing apparatus.

34. The process according to claim 3 further comprising:
($f_2$) after step (e), inducing at least a portion of the composition, a second portion, to flow into a passage of a second fluid processing apparatus;
($g_2$) injecting a high velocity transport fluid into the second portion of the composition through a nozzle communicating with the passage of the second fluid processing apparatus, whereby the transport fluid applies a shear force to the second portion of the composition such that the working fluid is atomised and a second vapour and droplet flow regime is formed downstream of the nozzle of the second fluid processing apparatus;
($h_2$) condensing the second vapour and droplet flow regime and transferring the second portion of the composition to a second holding vessel; and
($i_2$) holding the second portion of the composition in the second holding vessel at a second predetermined temperature for a second predetermined period of time, wherein the first fluid processing apparatus and first holding vessel, and the second fluid processing apparatus and second holding vessel operate in parallel; and the amylase enzyme is added to the first portion of the composition prior to the induction of the first portion of the composition into the passage of the first fluid processing apparatus, and the cellulase enzyme is added to the second portion of the composition prior to the induction of the second portion of the composition into the passage of the second fluid processing apparatus.

35. The process according to claim 34 further comprising:
($j_2$) cooling each portion of the composition to a predetermined fermentation temperature;
($k_2$) adding a fermentation agent to each portion of the composition;
($l_2$) transferring each portion of the composition to at least one fermentation vessel; and
($m_2$) holding each portion of the composition in the at least one fermentation vessel at the predetermined fermentation temperature for a predetermined fermentation time to form a fermented composition, which includes alcohol.

36. The process according to claim 35, wherein the fermentation temperature is between 30° C. and 40° C.

37. The according to claim 36, wherein the fermentation temperature is 35° C.

38. The process according to claim 35, wherein the fermentation agent is selected from the group consisting of a glucoamylase, a yeast, and combinations thereof.

39. The process according to claim 35, wherein the fermentation of the first and second portions of the composition is carried out in a single fermentation vessel.

40. The process according to claim 35, wherein the fermentation of the first and second portions of the composition is carried out in separate fermentation vessels.

41. The process according to claim 35 further comprising distilling the fermented composition to draw off the alcohol from the remainder of the composition.

42. The process according to claim 35 further comprising:
($n_2$) transferring any remaining non-fermented portions of the composition to a separator; and
($o_2$) separating solids from the remaining non-fermented portions of the composition.

43. The process according to claim 42 further comprising the steps of:
($p_2$) recovering the solids from the separator; and
($q_2$) returning the solids to the passage of the second fluid processing apparatus.

44. The process according to claim 42, wherein the second portion of the composition is the solids content recovered from the separator.

45. The process according to claim 5, wherein the transport fluid is steam.

46. The process according to claim 1, wherein the working fluid is water.

47. The process according to claim 1, wherein the biomass comprises one or more starch-based crops.

48. A process for producing bioethanol from a biomass comprising:
(a) inducing at least a first portion of a composition comprising biomass and a working fluid to flow into a passage of a fluid processing apparatus;
(b) injecting a high velocity transport fluid into the composition through a nozzle communicating with the passage of the fluid processing apparatus, whereby the transport fluid applies a shear force to the composition such that the working fluid is atomised and a vapour and droplet flow regime is formed downstream of the nozzle;
(c) condensing the vapour and droplet flow regime;
(d) transferring the composition to a first holding vessel;
(e) holding the composition in the first holding vessel at a first predetermined temperature for a first predetermined period of time, wherein a liquefaction enzyme is added to the composition prior to or during the process;
(f) transferring the composition to a second holding vessel following the end of the first predetermined period of time;
(g) holding the composition in the second holding vessel at a second predetermined temperature for a second predetermined period of time;
(h) cooling the composition to a predetermined fermentation temperature;
(i) adding a fermentation agent to the composition;
(j) transferring the composition to a fermentation vessel; and
(k) holding the composition in the fermentation vessel at the predetermined fermentation temperature for a predetermined fermentation time to generate a fermented composition, which comprises bioethanol.

* * * * *